United States Patent
Wagner et al.

(10) Patent No.: US 8,454,940 B2
(45) Date of Patent: Jun. 4, 2013

(54) MIXTURES COMPRISING BENZOTRIAZOLES AND MEROCYANINES

(75) Inventors: Barbara Wagner, Lörrach (DE); Oliver Reich, Grenzach-Wyhlen (DE); Alexander Mantler, Rheinfelden-Karsau (DE); Michael Schork, Riehen (CH)

(73) Assignee: BASF SE, Ludwigshafen (DE)

( * ) Notice: Subject to any disclaimer, the term of this patent is extended or adjusted under 35 U.S.C. 154(b) by 219 days.

(21) Appl. No.: 12/674,172

(22) PCT Filed: Aug. 18, 2008

(86) PCT No.: PCT/EP2008/060797
§ 371 (c)(1),
(2), (4) Date: Feb. 19, 2010

(87) PCT Pub. No.: WO2009/027258
PCT Pub. Date: Mar. 5, 2009

(65) Prior Publication Data
US 2011/0200540 A1    Aug. 18, 2011

(30) Foreign Application Priority Data
Aug. 24, 2007  (EP) ..................... 07114913

(51) Int. Cl.
*A61Q 17/04*   (2006.01)
*A61K 8/41*    (2006.01)
*A61K 8/37*    (2006.01)
*A61K 31/275*  (2006.01)
*A61K 8/31*    (2006.01)

(52) U.S. Cl.
USPC ............ 424/59; 424/70.9; 514/506; 514/579; 252/589

(58) Field of Classification Search
None
See application file for complete search history.

(56) References Cited

U.S. PATENT DOCUMENTS
2006/0257338 A1    11/2006    Bonda

FOREIGN PATENT DOCUMENTS

| EP | 1 649 902 A | 4/2006 |
|---|---|---|
| GB | 2 409 203 A | 6/2005 |
| WO | 00/25730 A | 5/2000 |
| WO | 2004/006878 A | 1/2004 |
| WO | 2006/032741 A | 3/2006 |
| WO | 2007/014848 A | 2/2007 |
| WO | WO 2007014848 A2 * | 2/2007 |

OTHER PUBLICATIONS

Printout from Scifinder for CAS registry No. 23328-53-2, 2-(2H-benzotriazol-2-yl)-6-dodecyl-4-methylphenol. Printed Apr. 18, 2012.*
"stabilized body care products, household products, textiles and fabrics" Nov. 5, 2003.
English Language Abstract of EP 1 649 902.

* cited by examiner

*Primary Examiner* — Frederick Krass
*Assistant Examiner* — Michael P Cohen
(74) *Attorney, Agent, or Firm* — Shiela A. Loggins

(57) ABSTRACT

The present invention relates to the use of a stabilizing composition comprising
(a) an effective stabilizing amount of at least one merocyanine derivative having an absorption maximum of 350 to 400 nm, and
(b) at least one UV filter selected from benzotriazole derivatives; and optionally
(c) at least one excited state quencher;
for the protection of body care and household products against the deleterious effects of light, heat and oxygen.

20 Claims, No Drawings

MIXTURES COMPRISING BENZOTRIAZOLES AND MEROCYANINES

The present invention relates to the use of merocyanine compounds having an absorption maximum of 350 to 400 nm and 2-hydroxyphenyl benzotriazole UV filters for the protection of body care and household products against the deleterious effects of light, heat and oxygen.

The present invention also relates to a mixture of at least one merocyanine having an absorption maximum of 350 to 400 nm and of at least one 2-hydroxyphenyl benzotriazole UV filter and optionally at least one excited state quencher.

Since consumers can choose from a large variety of Home & Personal Care products, producers need to communicate clearly how their brands are unique. Sophisticated products containing new fragrances and actives in many colourful formulations, displayed in transparent and translucent packaging are very common.

It is mandatory for commercial success that the pleasant appearance, product efficacy and the fresh smell of a consumer product will last during its whole product life cycle even when exposed heavily to UV-light. This exposure can result in decomposition processes and strong color fading destroying the product appearance, active ingredients and fragrances.

Various stabilization techniques of clear packaged products by absorption of UV light are commonly used and well known. For example broad-band UV light stabilizers of the benzotriazole class enhance product's stability and shelf live due to their very good UV-A and UV-B absorption properties.

The most effective stabilizers known as of today to prevent or delay light induced fading of transparent packaged products are e.g. benzotriazoles like known under the trade names Ciba TINOGARD HS or Ciba TINOGARD TL. These proved to be very effective, due to their broadband absorption properties and strong extinction in the UV-A range.

WO 2004/006878, WO 2005/058269, WO 2006/016806 A1, WO 2006/009451, WO 2006/125676 A1 and WO 2006/032741 A1 disclose merocyanine UV-A absorbers and their use for protecting human and animal hair and skin from UV radiation as well as their application in cosmetic and dermatological formulations.

WO 2007/014848 discloses various merocyanine structures which have superior properties in stabilizing cosmetic and dermatological formulations and household products.

These references also describe that the merocyanine UV absorbers can be mixed with any other UV filter substance.

It was now surprisingly found that the combination of specific merocyanine derivatives which have an absorption maximum in the range of 350 to 400 nm with benzotriazole UV-B filters and optionally with at least one excited state quencher have outstanding stabilizing properties.

Therefore, the present invention relates to the use of stabilizing composition comprising
(a) an effective stabilizing amount of at least one merocyanine derivative having an absorption maximum of 350 to 400 nm, and
(b) at least one UV filter selected from benzotriazole derivatives; and optionally
(c) at least one excited state quencher;
for the protection of body care and household products against the deleterious effects of light, heat and oxygen.

Examples of merocyanine compounds which correspond to component (a) are disclosed in WO 2004/006878, WO 2005/058269, WO 2006/016806 A1, WO 2006/009451, WO 2006/125676 A1, WO 2006/032741 A1 and WO 2007/081209.

The merocyanine compounds of component (a) preferably correspond to the compounds of formula

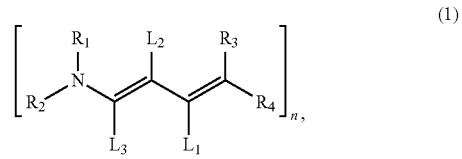

(1)

wherein
$R_1$ and $R_2$ independently of each other are hydrogen; $C_1$-$C_{22}$alkyl; $C_2$-$C_{22}$ alkenyl, $C_2$-$C_{22}$alkinyl, $C_3$-$C_{12}$cycloalkyl, $C_3$-$C_{12}$cycloalkenyl, $C_7$-$C_{20}$aralkyl, $C_1$-$C_{20}$heteroalkyl, $C_3$-$C_{12}$cycloheteroalkyl, $C_5$-$C_{11}$heteroaralkyl, $C_6$-$C_{20}$aryl, $C_4$-$C_9$heteroaryl, $COR_{13}$ or $CONR_{13}R_{14}$;

$R_3$ is CN; —$COOR_5$; —$CONHR_5$; —$COR_5$; or —$SO_2R_5$; —$CONR_5R_8$; $C_6$-$C_{20}$aryl or $C_4$-$C_9$ heteroaryl;

$R_4$ is CN; —$COOR_7$; —$CONHR_7$; —$COR_7$; —$SO_2R_7$; —$CONR_7R_8$; $C_1$-$C_{22}$ alkyl; $C_2$-$C_{22}$alkenyl; $C_2$-$C_{22}$ alkinyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl; $C_5$-$C_{11}$ heteroaralkyl; $C_6$-$C_{20}$ aryl; or $C_4$-$C_9$ heteroaryl;

$R_5$, $R_6$, $R_7$ and $R_8$ independently of each other are hydrogen; $C_1$-$C_{22}$alkyl; $C_2$-$C_{22}$alkenyl; $C_2$-$C_{22}$ alkinyl; $C_3$-$C_{12}$cycloalkyl; $C_3$-$C_{12}$cycloalkenyl; $C_7$-$C_{20}$aralkyl; $C_1$-$C_{20}$heteroalkyl, $C_3$-$C_{12}$cycloheteroalkyl; $C_5$-$C_{11}$heteroaralkyl; $C_6$-$C_{20}$aryl; or $C_4$-$C_9$heteroaryl; $SiR_{16}R_{16}R_{17}$; $Si(OR_{15})(OR_{16})(OR_{17})$; $SiR_{15}(OR_{15})(OR_{17})$; $SiR_{15}R_{16}(OR_{17})$; or a radical —XS;

$L_1$, $L_2$ or $L_3$ independently of each other are hydrogen, $C_1$-$C_{22}$alkyl; $C_2$-$C_{22}$alkenyl, $C_2$-$C_{22}$alkinyl; $C_3$-$C_{12}$cycloalkyl; $C_3$-$C_{12}$cycloalkenyl; $C_7$-$C_{20}$aralkyl; $C_1$-$C_{20}$heteroalkyl; $C_3$-$C_{12}$cycloheteroalkyl; $C_5$-$C_{11}$heteroaralkyl; $C_6$-$C_{20}$ aryl; $C_4$-$C_9$heteroaryl; CN; OH; $OR_9$; or $COOR_9$;

$R_9$ is hydrogen; $C_1$-$C_{22}$alkyl; $C_2$-$C_{22}$alkenyl; $C_2$-$C_{22}$alkinyl; $C_3$-$C_{12}$cycloalkyl; $C_3$-$C_{12}$ cycloalkenyl; $C_7$-$C_{20}$aralkyl; $C_1$-$C_{20}$heteroalkyl; $C_3$-$C_{12}$cycloheteroalkyl; $C_6$-$C_{11}$heteroaralkyl; $C_6$-$C_{20}$ aryl; or $C_4$-$C_9$ heteroaryl;

$L_1$ and $L_2$, $L_1$ and $L_3$, $L_2$ and $L_3$, $L_1$ and $R_4$, $L_2$ and $R_4$, $L_1$ and $R_1$, $L_2$ and $R_1$, $L_3$ and $R_1$, $L_3$ and $R_5$, $R_3$ and $R_4$, $R_1$ and $R_2$, $R_7$ and $R_8$, $R_5$ and $R_6$ may be linked together to form 1, 2, 3 or 4 carbocyclic or N, O and/or S-heterocyclic rings, which may be further fused with other aromatic rings. Each N in a N-heterocyclic ring can be unsubstituted or substituted by $R_{10}$; each alkyl, alkenyl, alkinyl, cycloalkyl or cycloalkylen group may be unsubstituted or substituted independently of one another by one or more $R_{11}$; and each aryl, heteroaryl, aralkyl, arylen, heteroarylen or aralkylen may be unsubstituted or substituted by one or more $R_{12}$, wherein $R_{10}$ represents $R_{13}$; $COR_{13}$, $COOR_{13}$; $CONH_2$; $CONHR_{13}$; or $CONR_{13}R_{14}$;

$R_{11}$ represents halogen; OH; $NH_2$; $NHR_{15}$; $NR_{15}R_{16}$; $NR_{15}OR_{16}$; O—$R_{15}$; C—CO—$R_{15}$; S—$R_{15}$; CO—$R_{10}$; oxo; thiono; CN; COOH; $CONH_2$; $COOR_{15}$; $CONHR_{15}$; $CONR_{16}R_{16}$; $SO_2NH_2$; $SO_2NHR_{15}$, $SO_2NR_{15}R_{16}$; $SO_2R_{15}$; $SO_3R_{15}$; $SiR_{15}R_{16}R_{17}$, $SiOR_{15}(OR_{16})(OR_{17})$; $SiR_{15}(OR_{16})(OR_{17})$; $SiR_{15}R_{16}(OR_{17})$, O—Si—$R_{15}R_{16}R_{17}$; O—Si—$OR_{15}(OR_{16})(OR_{17})$; O—Si—$R_{15}R_{16}(OR_{17})$; O—$SiR_{15}(OR_{16})(OR_{17})$; $PO(OR_{15})(OR_{16})$; or a radical XS;

$R_{12}$ represents halogen, CN, SH, OH, CHO, $R_{18}$; $OR_{18}$; $SR_{18}$; $C(R_{18})=CR_{19}R_{20}$; $O-CO-R_{19}$; $NHR_{19}$; $NR_{18}R_{19}$; $CONH_2$; $CONHR_{18}$; $CONR_{18}R_{19}$; $SO_2NH_2$; $SO_2NHR_{18}$; $SO_2NR_{18}R_{19}$; $SO_2R_{18}$; $COOH$; $COOR_{18}$; $OCOOR_{16}$; $NHCOR_{18}$; $NR_{18}COR_{19}$; $NHCOOR_{19}$; $NR_{19}COOR_{20}$; $SiR_{15}R_{16}R_{17}$; $SiOR_{16}(OR_{16})(OR_{17})$; $SiR_{15}(OR_{16})(OR_{17})$; $SiR_{15}R_{16}(OR_{17})$; $OSiR_{15}R_{16}R_{17}$; $OSiOR_{15}(OR_{16})(OR_{17})$; $OSiR_{15}R_{16}(OR_{17})$; $OSiR_{15}(OR_{16})(OR_{17})$; $P(=O)OR_{19}OR_{20}$; $P(=O)R_{19}OR_{20}$; $P(=O)R_{19}R_{20}$; or a radical $-XS$; or is selected from the group consisting of $C_1-C_{12}$alkyl; $C_3-C_{12}$cycloalkyl; $C_1-C_{12}$alkenyl; $C_3-C_{12}$cycloalkenyl; $C_1-C_{12}$alkylthio; $C_3-C_{12}$cycloalkylthio; $C_1-C_{12}$alkenylthio; $C_3-C_{12}$cycloalkenylthio; $C_1-C_{12}$alkoxy; $C_3-C_{12}$cycloalkoxy; $C_1-C_{12}$alkenyloxy; or $C_3-C_{12}$cycloalkenyloxy, which may be unsubstituted or substituted by one or more, identical or different $R_{11}$;

$R_{13}$, $R_{14}$, $R_{15}$, $R_{16}$, $R_{17}$, $R_{18}$, $R_{19}$ and $R_{29}$ are independently of each other $C_1-C_{22}$alkyl; $C_3-C_{12}$cycloalkyl; $C_2-C_{12}$alkenyl; $C_3-C_{12}$cycloalkenyl; $C_6-C_{14}$aryl; $C_4-C_{12}$heteroaryl; $C_7-C_{18}$aralkyl or $C_5-C_{16}$heteroaralkyl; or $R_{13}$ and $R_{14}$, $R_{15}$ and $R_{16}$, $R_{16}$ and $R_{17}$ and/or $R_{18}$ and $R_{19}$ may be linked together to form unsubstituted or with $C_1-C_4$alkyl substituted pyrrolidin, piperidin, piperazin or morpholin;

X represents a linker;

S signifies a silane-, oligosiloxane- or polysiloxane-moiety;

the term "oligosiloxane" denotes a group of the general formula $Si(R_{15})_m[OSi(R_{16})]_o$ wherein m has a value of 0, 1 or 2, o has a value of 3, 2 or 1; and m+o have a value of 3 or refers to groups of the general formula

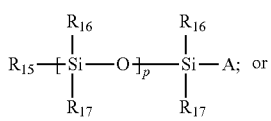

(1a)

wherein

A represents a bond to the linker X; and p has a value of 1 to 9;

the term "polysiloxane" refers in this context to groups of the general formula

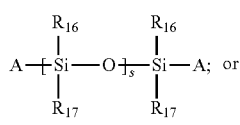

(1c)

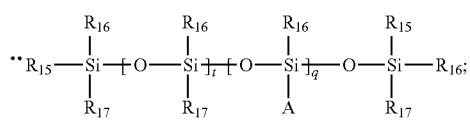

(1d)

wherein

A represents a bond to the linker X;

s has a value of 4 to 250;

t has a value of 5 to 250;

q has a value of 1 to 30;

n is 1 or integer;

when n=2, $R_1$, $R_5$ or $R_4$ is a bivalent alkyl group; or $R_1$ and $R_2$ together with the 2 nitrogen atoms linking them form a unsubstituted or alkyl-substituted

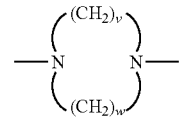

-ring;

v is from 1 to 4, w is from 1 to 4;

when n=3, $R_1$, $R_5$ or $R_4$ is a trivalent alkyl group;

when n=4, $R_1$, $R_5$ or $R_4$ is a tetravalent alkyl group; and $R_1$ and $R_2$ in formula (I) are not simultaneously hydrogen.

Halogen is chloro, bromo, fluoro or iodo, preferably fluoro, more preferably fluoroalkyl (for example trifluormethyl, α,α, α-trifluorethyl or perfluorinated alkyl groups like heptafluorpropyl).

Alkyl, cycloalkyl, alkenyl, alkylidene or cycloalkenyl residues can be straight-chain or branched, or also monocyclic or polycyclic.

Alkyl can be for example methyl, straight-chain $C_2-C_{22}$alkyl or preferably branched $C_3-C_{22}$alkyl.

Alkenyl can be e.g. straight-chain $C_2-C_{22}$alkenyl or preferably branched $C_3-C_{22}$alkenyl.

$C_1-C_{22}$alkyl is for example methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-octyl, 1,1,3,3-tetramethylbutyl, 2-ethylhexyl, nonyl, decyl, n-octadecyl, eicosyl, cetyl-, myristyl- or dodecyl.

$C_3-C_{12}$cycloalkyl is for example cyclopropyl, cyclobutyl, cyclopentyl, cyclohexyl, trimethylcyclohexyl, menthyl, thujyl, bornyl, 1-adamantyl oder 2-adamantyl.

$C_2-C_{22}$alkenyl or $C_3-C_{12}$cycloalkenyl refers to unsaturated hydrocarbon residues containing one or multiple double bonds such vinyl, allyl, 2-propene-2-yl, 2-butene-1-yl, 3-butene-1-yl, 1,3-butadiene-2-yl, 2-cyclobutene-1-yl, 2-pentene-1-yl, 3-pentene-2-yl, 2-methyl-1-butene-3-yl, 2-methyl-3-butene-2-yl, 3-methyl-2-butene-1-yl, 1,4-pentadiene-3-yl, 2-cyclopentene-1-yl, 2-cyclohexene-1-yl, 3-cyclohexene-1-yl, 2,4-cyclohexadiene-1-yl, 1-p-menthene-8-yl, 4(10)-thujen-10-yl, 2-norbornene-1-yl, 2,5-norbornadiene-1-yl, 7,7-dimethyl-2,4-norcaradiene-3-yl or signifies different isomers of hexenyl, octenyl, nonenyl, decenyl or dodecenyl.

$C_7-C_{20}$aralkyl is for example benzyl, 2-benzyl-2-propyl, 13-phenyl-ethyl, 9-fluorenyl, α,α-dimethylbenzyl, ω-phenyl-butyl, ω-phenyl-octyl, ω-phenyl-dodecyl oder 3-methyl-5-(1',1',3',3'-tetramethyl-butyl)-benzyl.

A $C_7-C_{20}$aralkyl moiety can be unsubstituted or substituted at the alkyl- as well at the aryl-moiety of the aralkyl-group, but preferably substituted at the aryl-moiety.

$(C_1-C_6)$-alkylidene signifies for example methylene, ethyl-1-ene, propyl-2-ene.

$C_6-C_{20}$aryl is for example phenyl, naphthyl, biphenylyl, 2-fluorenyl, phenanthryl, anthracenyl oder terphenylyl.

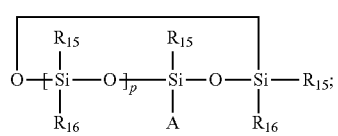

(1b)

$C_4$-$C_{12}$heteroaryl signifies a unsaturated or aromatic radical with 4n+2 conjugated π-electrons, such as 2-thienyl, 2-furyl, 2-pyridyl, 2-thiazolyl, 2-oxazolyl, 2-imidazolyl, isothiazolyl, triazolyl or any other ring system consisting of thiophene-, furan-, pyridine, thiazol, oxazol, imidazol, isothiazol, triazol, pyridine- and phenyl rings, which are unsubstituted or substituted with 1 to 6 ethyl, methyl, ethylen and/or methylen groups, such as benzotriazolyl.

$C_5$-$C_{16}$heteroaralkyl signifies for example a $C_1$-$C_8$ alkyl moiety which is substituted with a $C_4$-$C_8$heteroaryl group.

Preferably merocyanines of formula (I) are used, wherein
$R_1$ and $R_2$ independently of each other are hydrogen; or $C_1$-$C_{22}$alkyl; or $COR_{13}$
$R_3$ and $R_4$ are independently of each other CN; or —$COOR_5$; or —$SO_2R_5$; or —$CONR_5R_6$
$R_5$ is hydrogen; $C_1$-$C_{22}$alkyl; $C_6$-$C_{20}$aryl; or a radical *—X—S;
$L_1$, $L_2$ or $L_3$ independently of each other are hydrogen; or $C_1$-$C_{22}$alkyl; or $L_1$ and $L_2$, $L_1$ and $L_3$, $L_2$ and $L_3$, may be linked together to form a carbocyclic ring comprising 6 to 10 carbon atoms, which may be further fused with other aromatic rings; and which may be further substituted by one or more than one $C_1$-$C_4$alkyl;
X represents a linker;
S refers to groups of the general formula

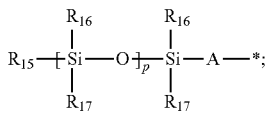

(2a)

wherein
$R_{16}$ and $R_{17}$ independently from each other are the radical —OSi($R_{17}$)(($R_{18}$)($R_{19}$);
$R_{16}$ and $R_{17}$ independently of each other are $C_1$-$C_{22}$alkyl;
A represents a bond to the linker X; and
p has a value of 1 to 9.

More preferably merocyanines of formula

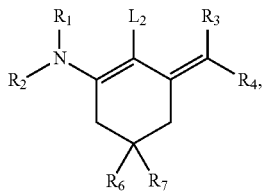

(2)

are used, wherein
$R_1$ and $R_2$, independently from each other are hydrogen; or $C_1$-$C_{12}$alkyl;
$L_2$ is hydrogen;
$R_3$ is $COOR_5$; or —CN;
$R_4$ is —CN; and
$R_5$ is $C_1$-$C_{22}$alkyl;
$R_6$ and $R_7$ independently from each other are hydrogen; or $C_1$-$C_3$alkyl.

Furthermore, more preferably merocyanines of formula

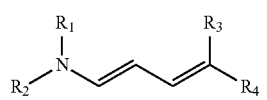

(3)

are used, wherein
$R_1$ and $R_2$, independently from each other are hydrogen; or $C_1$-$C_{12}$alkyl;
$R_3$ is —CN; or —$COOR_5$;
$R_4$ is —CN; or —$COOR_6$; or —$SO_2R_6$;
$R_5$ is $C_1$-$C_{22}$alkyl;
$R_6$ is $C_1$-$C_{22}$alkyl; or $C_6$-$C_{20}$aryl;

Particularly preferred merocyanine compounds as used in the present invention as component (a) are listed in the Table 1 below:

TABLE 1

Examples of preferred Merocyanine compounds (MC-01)

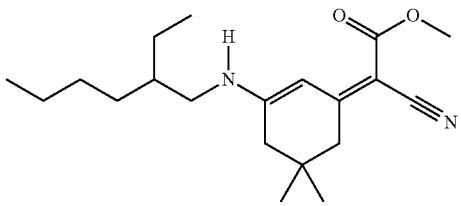

E/Z-isomers (MC-02)

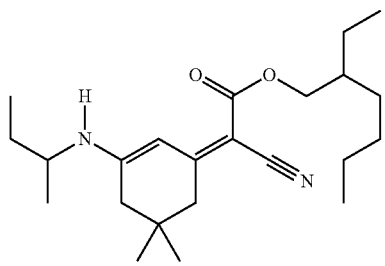

E/Z-isomers

TABLE 1-continued
Examples of preferred Merocyanine compounds
(MC-03)
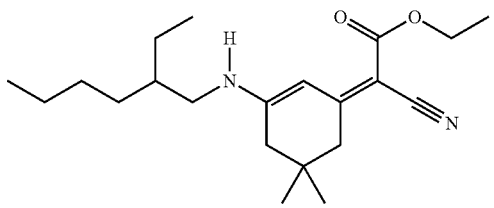
E/Z-isomers
(MC-04)
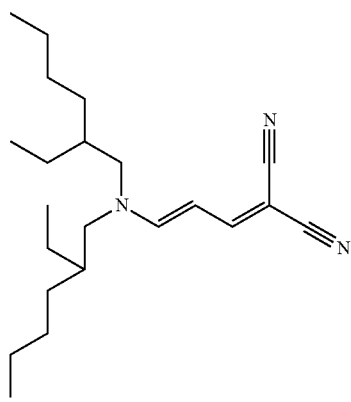
E/Z-isomers
(MC-05)
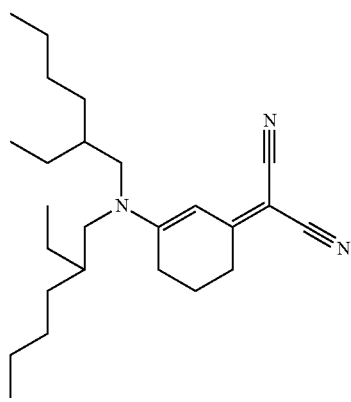 [SMILES: CCCCC(CC)CN(CC(CC)CCCC)C1=CC(=C(C#N)C#N)CCC1]
(MC-06)
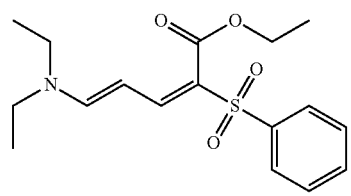
CAS-No. 160306-22-9

TABLE 1-continued
Examples of preferred Merocyanine compounds
(MC-07)
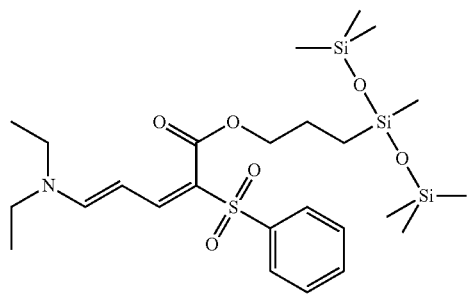
E/Z-isomers
(MC-08)
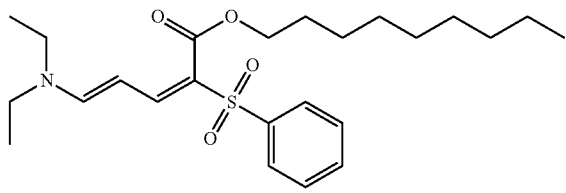
CAS-No. 98835-90-6
(MC-09)
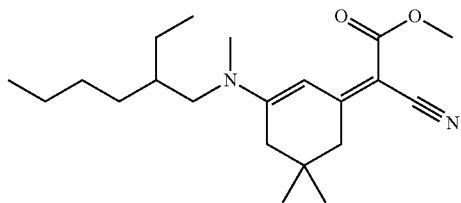
E/Z-isomers
(MC-10)
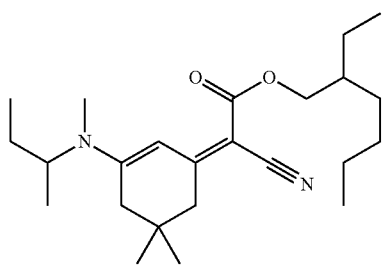
E/Z-isomers
(MC-11)
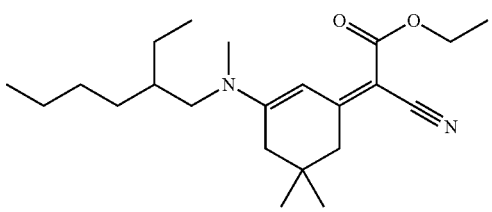
E/Z-isomers TABLE 1-continued Examples of preferred Merocyanine compounds (MC-12) 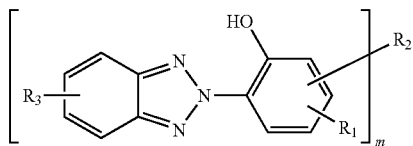

Examples of benzotriazole UV filters (component (b)) are disclosed in WO 00/25730, WO 03070819, EP 1342748, WO 9406404 A1 and EP 796613 A1.

Preferably benzotriazole derivatives of formula

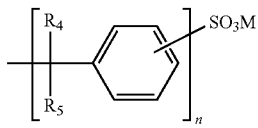 (4)

are used, wherein
$R_1$ is $C_1$-$C_{30}$alkyl; $C_1$-$C_5$alkoxy; $C_1$-$C_5$alkoxycarbonyl; $C_5$-$C_7$cycloalkyl; $C_6$-$C_{10}$aryl; aralkyl; —$SO_3M$; or a radical of formula

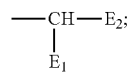 (4a)

$R_3$ is hydrogen; $C_1$-$C_5$alkyl; $C_1$-$C_5$alkoxy; halogen, preferably Cl; or hydroxy;
$R_4$ and $R_5$ are each independently of the other hydrogen; or $C_1$-$C_5$alkyl;
m is 1 or 2;
n is 0 or 1;
if m=1,
$R_2$ is hydrogen; unsubstituted or phenyl-substituted $C_1$-$C_{12}$alkyl; or $C_6$-$C_{10}$aryl;
if m=2,
$R_2$ is the direct bond; or —$(CH_2)_p$—; and
p is 1 to 3.

More preferably the benzotrizoles as used in the present invention correspond to the formula

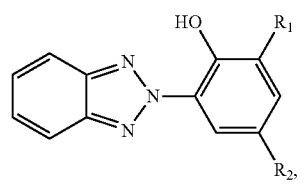 (5)

wherein
$R_1$ is a random statistical mixture of at least three isomeric branched secondary alkyl groups each having 8 to 30 carbon atoms and having the formula $$—\underset{\underset{E_1}{|}}{CH}—E_2;$$

$E_1$ is a straight-chain $C_1$-$C_{14}$alkyl;
$E_2$ is a straight-chain $C_4$-$C_{15}$alkyl; wherein the total number of carbon atoms in $E_1$ plus $E_2$ is from 7 to 29; and
$R_2$ is $C_1$-$C_5$alkyl.

Most preferred is the benzotriazole derivative 2-(2H-benzotriazol-2-yl)-6-dodecycl-4-methylphenol which corresponds to the formula

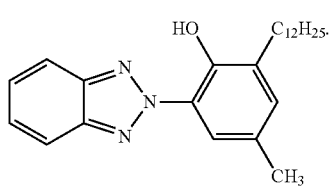 (BT-01)

Particularly preferred benzotriazole compounds (component (b)) are listed in Table 2 below:

TABLE 2

Examples of preferred benzotriazole compounds

BT-01

CAS-No.: 125304-04-3

TABLE 2-continued
Examples of preferred benzotriazole compounds
BT-02
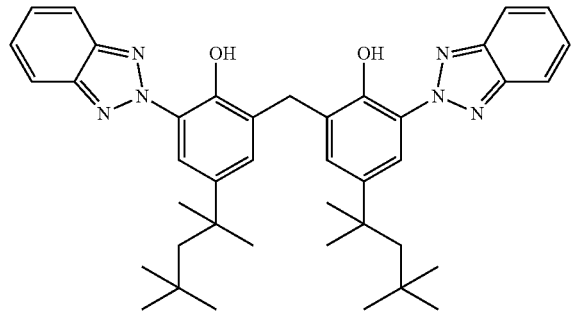 [SMILES: CC(C)(C)CC(C)(C)c1cc(Cc2cc(C(C)(C)CC(C)(C)C)cc(-n3nc4ccccc4n3)c2O)c(O)c(-n2nc3ccccc3n2)c1]
BT-03
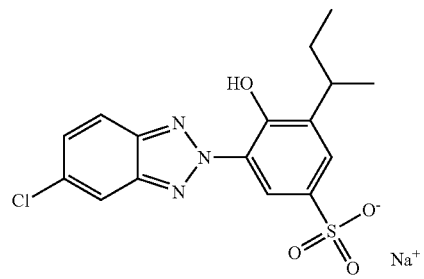
CAS-No.: 92484-48-5
BT-04
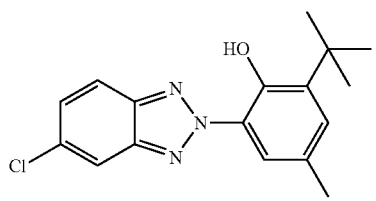
CAS-No.: 3896-11-5
BT-05
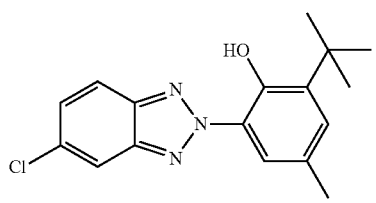
CAS-No.: 3896-11-5
BT-06
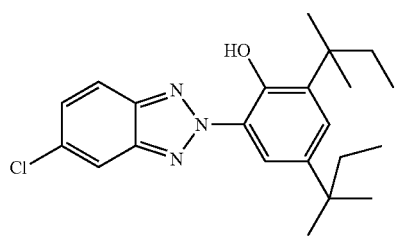 [SMILES: CCC(C)(C)c1cc(-n2nc3ccc(Cl)cc3n2)c(O)c(C(C)(C)CC)c1]

The stabilized composition of the present invention may additionally comprise an Excited State Quencher (ESQ™) (=component (c)). It interacts with high-energy states of molecules, e.g. caused by UV-radiation or visible light, and significantly reduces the probability of degradation reactions and scavengers radical intermediates. This mechanism works complimentarily to that of UV light stabilizers.

Examples of excited state quenchers selected from the group of hindered amine stabilizers are disclosed in the patent applications WO 01/07550, WO 2005/042828 A2 and U.S. Pat. No. 6,254,724.

Particularly preferred hindered amine stabilizers are
($c_1$) hindered nitroxyl compounds of formula

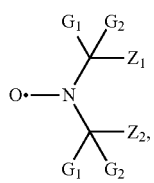

(6a)

($c_2$) hindered hydroxylamine compounds of formula

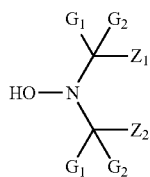

(6b)

and
($c_3$) hindered hydroxylamine salt compounds of formula

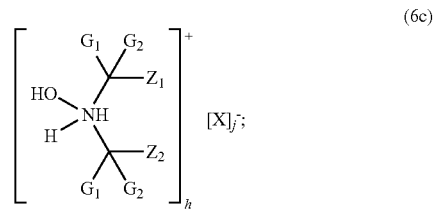

(6c)

wherein
$G_1$ and $G_2$ are independently alkyl of 1 to 4 carbon atoms or are together pentamethylene,
$Z_1$ and $Z_2$ are each methyl, or $Z_1$ and $Z_2$ together form a linking moiety which may additionally be substituted by an ester, ether, hydroxy, oxy, oxo, cyanohydrin, amide, amino, carboxy or urethane group,
X is an inorganic or organic anion, such as phosphate, phosphonate, carbonate, bicarbonate, nitrate, chloride, bromide, bisulfate, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylene-diaminetetraacetic acid or of diethylenetriaminepentaacetic acid, a diethylenetriaminepentamethylenephosphonate, an alkylsulfonate or an arylsulfonate, and
where the total charge of cations h is equal to the total charge of anions j.

Examples of particularly preferred excited state stabilizers are listed in Table 3 below:

TABLE 3

Preferred excited state stabilizers

ESS-01

ESS-02

ESS-03

TABLE 3-continued

Preferred excited state stabilizers

ESS-04

[Structure: bis(2,2,6,6-tetramethylpiperidin-4-yl) derivative with —OCOCH₂CH₂CH₂CH₂— linker], subscript 2

ESS-05

[Structure: bis(1-octyloxy-2,2,6,6-tetramethylpiperidin-4-yl) sebacate-type diester with —(CH₂)₈— linker; N—OC₈H₁₇ on each piperidine]

ESS-06

[Structure: 2-cyano-3,3-diphenylacrylate, isooctyl ester]

Octocrylene
CAS 6197-30-4

ESS-07

[Structure: ethyl 2-cyano-3,3-diphenylacrylate]

CAS 5232-99-5

ESS-08

[Structure: 2,6-naphthalenedicarboxylic acid, diisooctyl ester]

Hallbrite TQ
CAS 127474-91-3

ESS-09

Polycrylene
CAS 866102-82-1

ESS-10

[Structure: bis(1-hydroxy-2,2,6,6-tetramethylpiperidin-4-yl) sebacate with —(CH₂)₈— linker; N—OH on each piperidine]

CAS #30538-92-2

Combinations of excited state stabilizers like the compound (ESS-01) with UV absorbers like other Tinogard UV light stabilizers show a synergistic stabilizing effect.

This "boosting" effect allows for high demanding shelf life enhancements as well as cost effective ingredient protection.

In the literature also excited state quenchers based on the naphthalene structure are known.

Particularly preferred are dialkyl naphthalates structures such as disclosed US 2002/197285, US 2006/228311 and WO 2002/087528.

Another group of particularly preferred excited state quenchers are those based on the β,β-diphenylacrylate structure which are for example described in US 2004/047818, US 2006/257338, US 2006/228311, US 2004/062726 and US 2004/057916.

The stabilizing composition comprising
(a) an effective stabilizing amount of at least one merocyanine derivative having an absorption maximum of 350 to 400 nm,
(b) at least one UV filter selected from benzotriazole derivatives; and optionally
(c) at least one excited state quencher;
is novel and represents a further subject matter of the present invention.

Particularly preferred mixtures are listed in Table 4 below:

TABLE 4

Preferred Combinations

| | Component (a) | Component (b) |
|---|---|---|
| M1 | 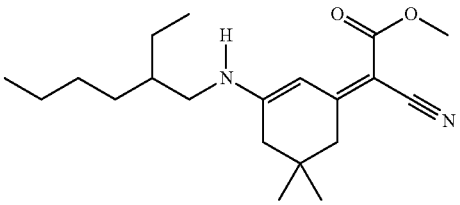<br>E/Z-isomers<br>MC-01 | 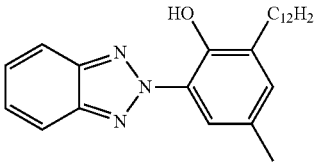<br>CAS-No.: 125304-04-3<br>BT-01 |
| M1A | 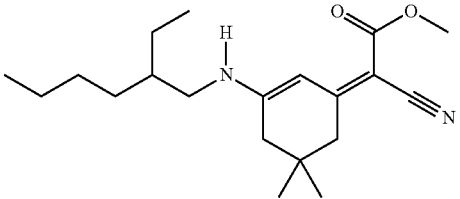<br>E/Z-isomers<br>MC-01 | 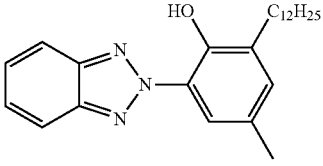<br>CAS-No.: 125304-04-3<br>BT-01 |
| M2 | 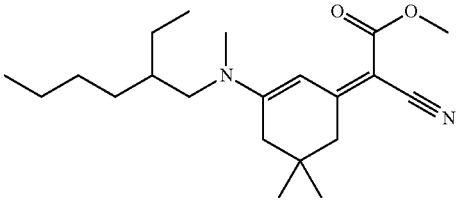<br>E/Z-isomers<br>MC-09 | 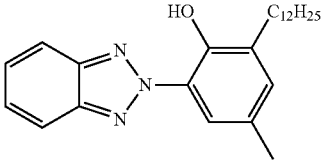<br>CAS-No.: 125304-04-3<br>BT-01 |
| M2A | 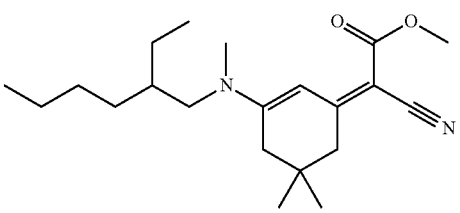<br>E/Z-isomers<br>MC-09 | 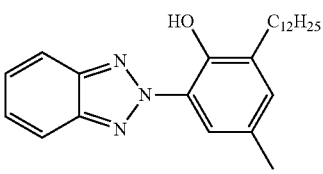<br>CAS-No.: 125304-04-3<br>BT-01 |

TABLE 4-continued
| | | |
|---|---|---|
| M3 | 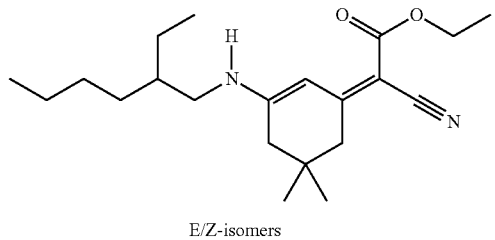<br>E/Z-isomers<br>MC-03 | 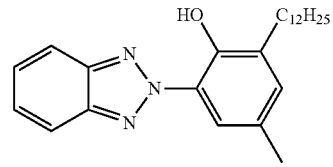<br>CAS-No.: 125304-04-3<br>BT-01 |
| M3A | 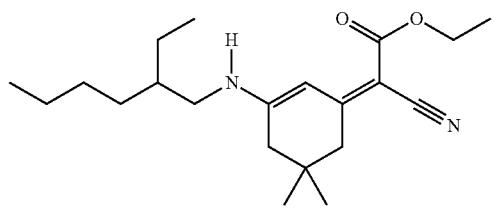<br>E/Z-isomers<br>MC-01 | 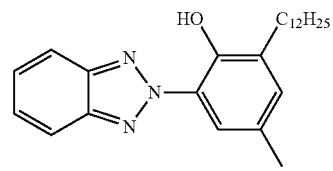<br>CAS-No.: 125304-04-3<br>BT-01 |
| M4 | 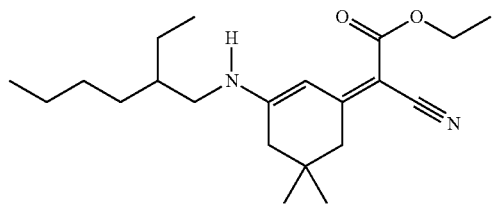<br>E/Z-isomers<br>MC-03 | 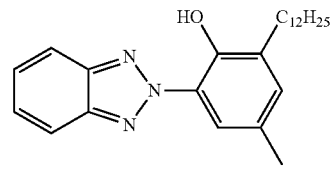<br>CAS-No.: 125304-04-3<br>BT-01 |
| M4A | 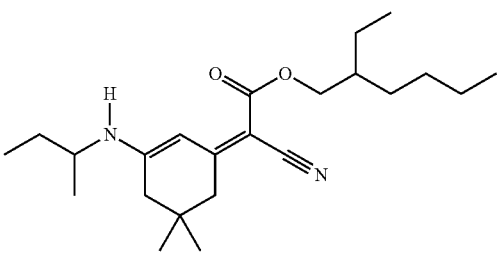<br>E/Z-isomers<br>MC-02 | 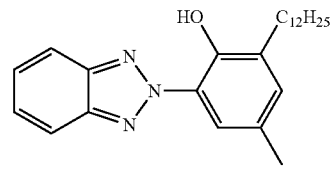<br>CAS-No.: 125304-04-3<br>BT-01 |
| M5 | 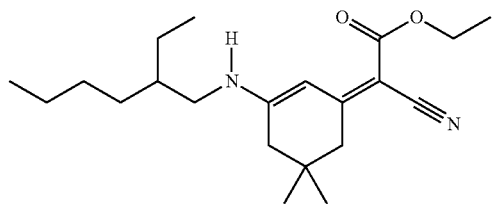<br>E/Z-isomers<br>MC-03 | 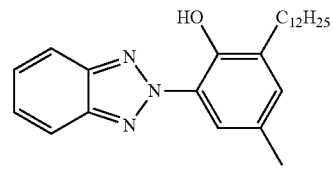<br>CAS-No.: 125304-04-3<br>BT-01 |

TABLE 4-continued
| | | |
|---|---|---|
| M6 | 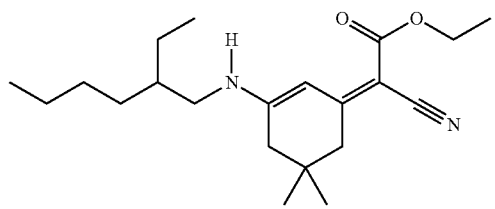 [SMILES: CCCCC(CC)CNC1=C/C(=C(/C#N)C(=O)OCC)CC(C)(C)C1]<br>E/Z-isomers<br>MC-03 | 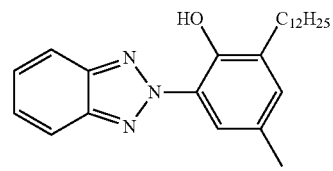<br>CAS-No.: 125304-04-3<br>BT-01 |
| M7 | 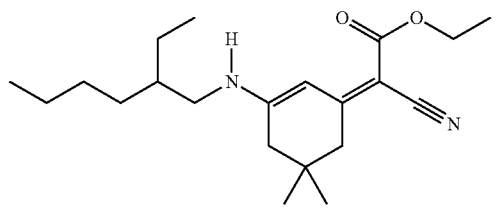<br>E/Z-isomers<br>MC-03 | 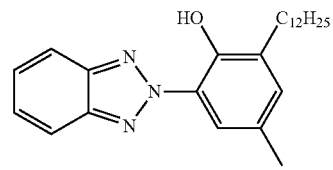<br>CAS-No.: 125304-04-3<br>BT-01 |
| M8 | 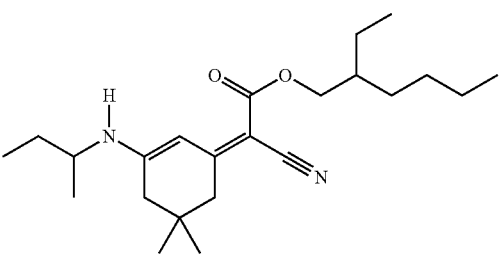<br>E/Z-isomers<br>MC-02 | 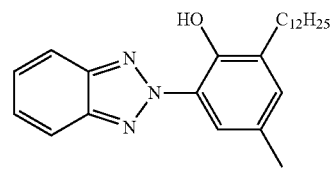<br>CAS-No.: 125304-04-3<br>BT-01 |
| M9 | 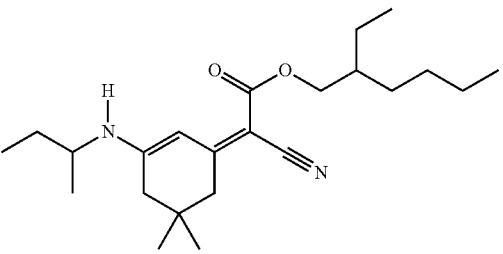<br>E/Z-isomers<br>MC-02 | 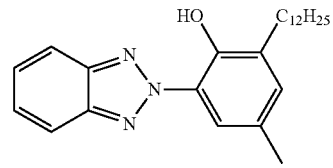<br>CAS-No.: 125304-04-3<br>BT-01 |
| M10 | 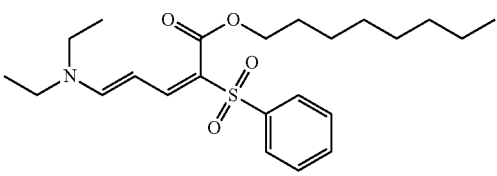<br>E/Z-isomers<br>MC-08 | 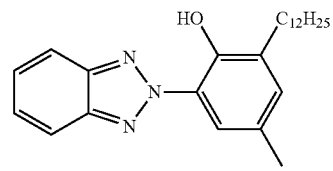<br>CAS-No.: 125304-04-3<br>BT-01 |

TABLE 4-continued
| | | | |
|---|---|---|---|
| (M10A) | 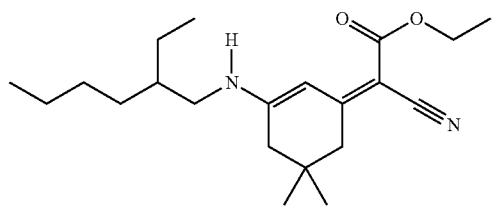 | 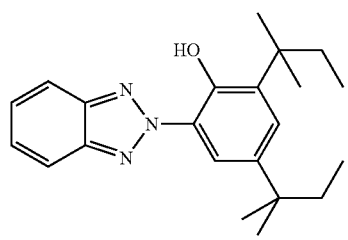 | |
| | | Tinuvin 328 BC-06 | |
| M11 | 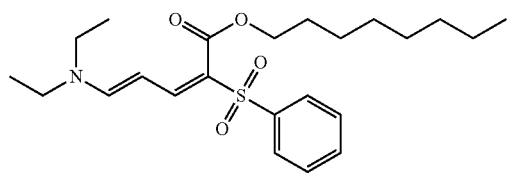 [SMILES: CCCCCCCCOC(=O)/C(=C\C=C\N(CC)CC)S(=O)(=O)c1ccccc1] | 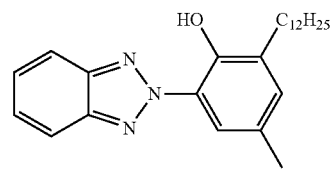 | |
| | | CAS-No.: 125304-04-3 BT-01 | |
| M12 | 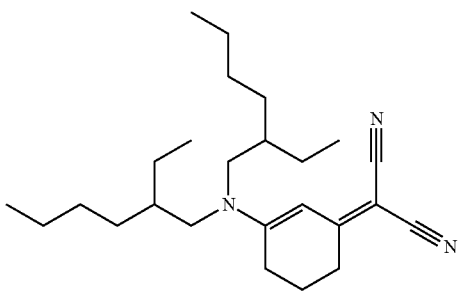 | 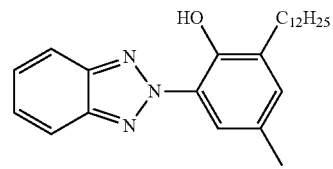 | |
| | MC-05 | CAS-No.: 125304-04-3 | |
| M13 | 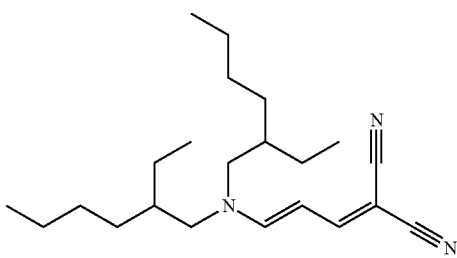 | 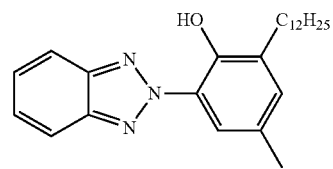 | |
| | MC-04 | CAS-No.: 125304-04-3 BT-01 | |
| (M14) | 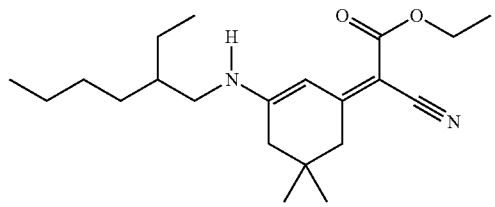 | 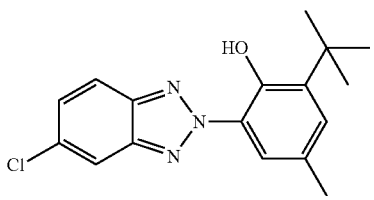 | |
| | E/Z-isomers MC-03 | BT-04 | |

TABLE 4-continued
(M15) 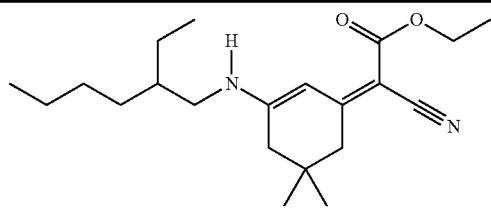
E/Z-isomers
MC-03
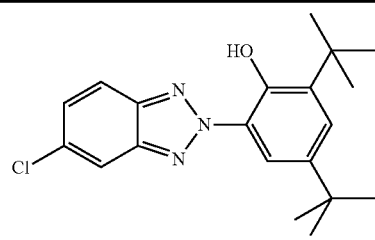
BT-07
(M16) 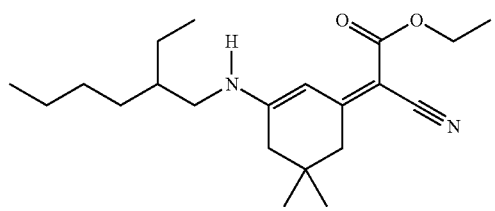
E/Z-isomers
MC-03
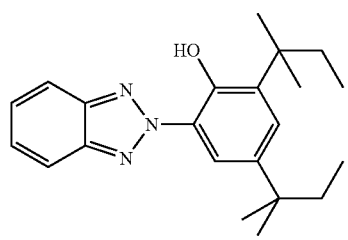
Tinuvin 328
BC-06
(M17) 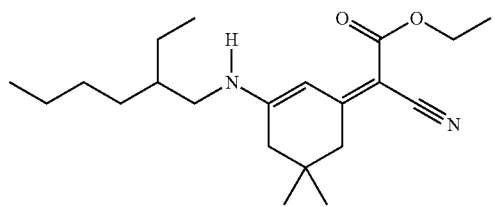
E/Z-isomers
MC-03
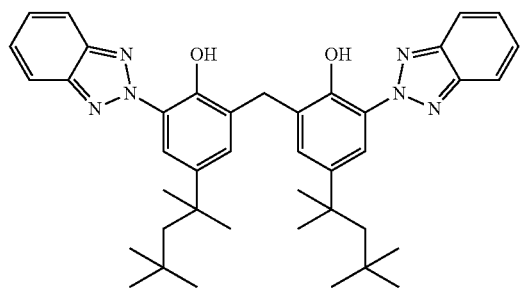
BT-02
(M18) 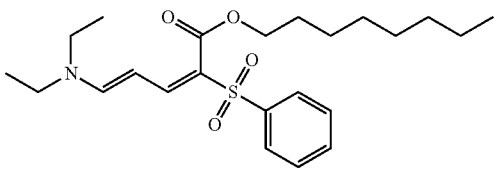
E/Z-isomers
MC-08
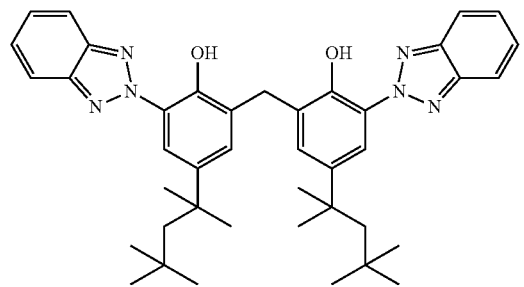
BT-02
(M19) 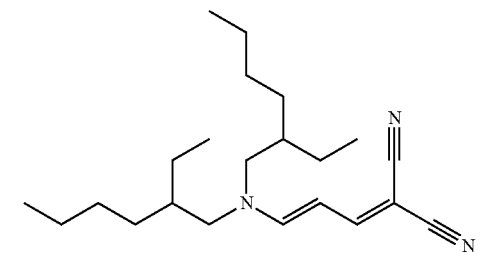
E/Z-isomers
MC-04
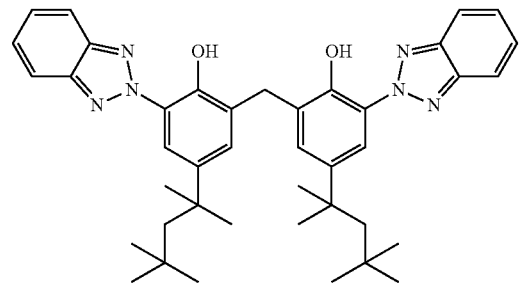
BT-02

TABLE 4-continued
(M20) 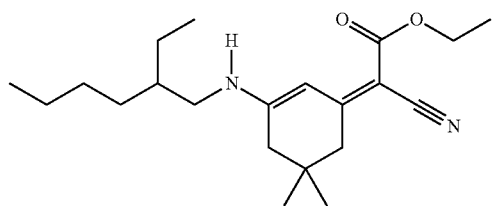
E/Z-isomers
MC-03
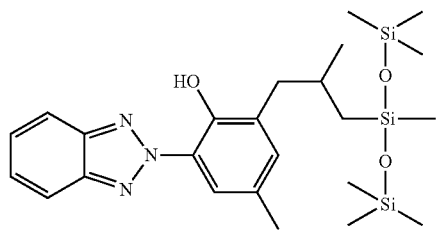
CAS-No.: 155633-54-8
BT-03
(M21) 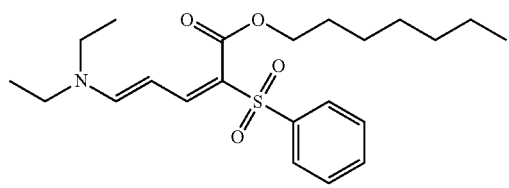
E/Z-isomers
MC-08
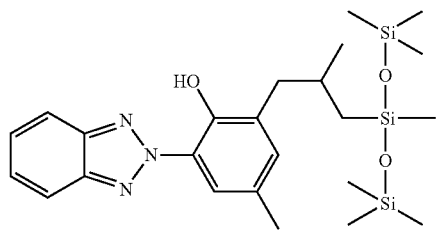
CAS-No.: 155633-54-8
BC-03
(M22) 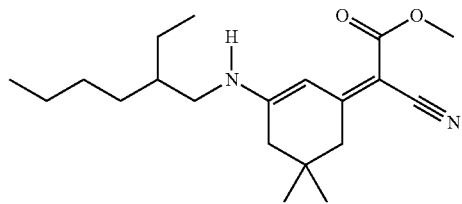
E/Z-isomers
MC-01
and
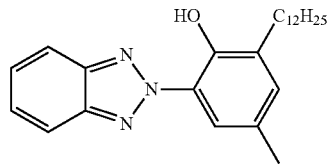
CAS-No.: 125304-04-3
BT-01
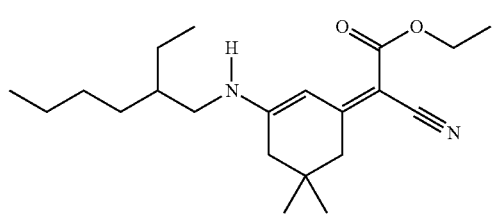
E/Z-isomers
MC-09

TABLE 4-continued
(M23)
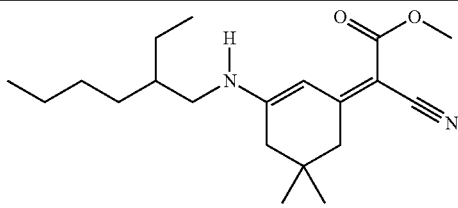
E/Z-isomers
MC-01
and
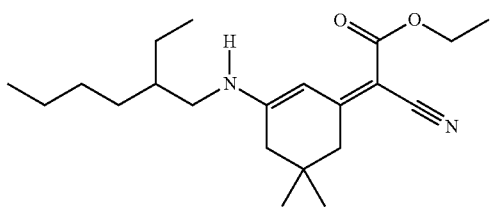
E/Z-isomers
MC-03
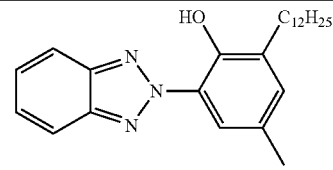
CAS-No.: 125304-04-3
BT-01
| | Component (c) |
|---|---|
| M1 | |
| M1A | 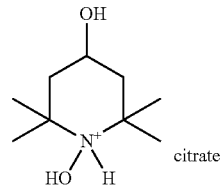 citrate |
| M2 | |
| M2A | 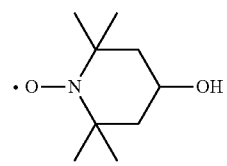 |
| M3 | |
| M3A | 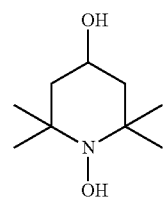 |
| M4 | 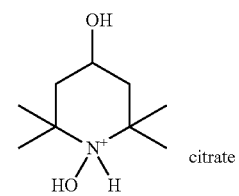 citrate |
ESS-01

TABLE 4-continued
M4A
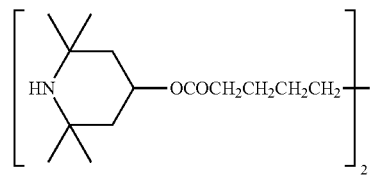
M5
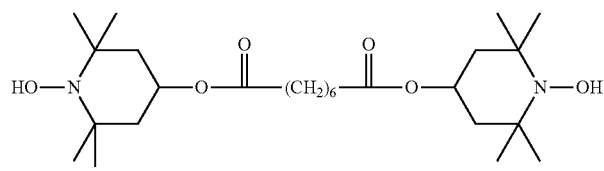
CAS # 30538-92-2
ESS-06
M6
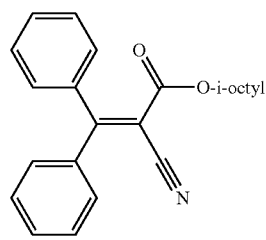
Octocrylene
CAS 6197-30-4
ESS-02
M7
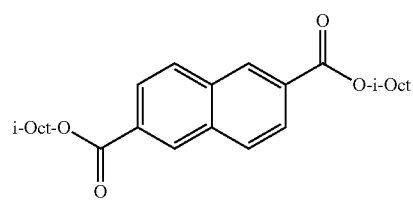
Hallbrite TQ
CAS 127474-91-3
ESS-04
M8
M9
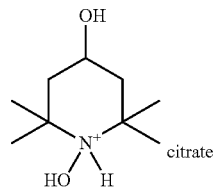
ESS-01
M10
(M10A)
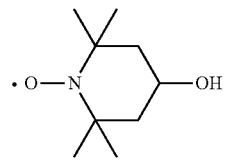

| | |
|---|---|
| M11 | 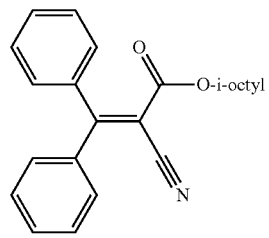<br>Octorylene<br>CAS 6297-30-4<br>ESS-02 |
| M12 | |
| M13 | |
| (M14) | |
| (M15) | |
| (M16) | |
| (M17) | |
| (M18) | |
| (M19) | |
| (M20) | |
| (M21) | |
| (M22) | |
| (M23) | |

The stabilizing composition of the present invention is particularly suitable for protecting body-care and household products against photolytic degradation.

Personal Care Uses

The stabilizing composition of the present invention may be used as single component or in mixture with other stabilizers in particular for skin-care products, bath and shower additives, preparations containing fragrances and odoriferous substances, hair-care products, dentifrices, deodorizing and antiperspirant preparations, decorative preparations, light protection formulations and preparations containing active ingredients.

Skin-care products are, in particular, body oils, body lotions, body gels, treatment creams, skin protection ointments, shaving preparations, such as shaving foams or gels, skin powders, such as baby powder, moisturizing gels, moisturizing sprays, revitalizing body sprays, cellulite gels and peeling preparations.

Suitable bath and shower additives are shower gels, bath-salts, bubble baths and soaps.

Preparations containing fragrances and odoriferous substances are in particular scents, perfumes, toilet waters and shaving lotions (aftershave preparations).

Suitable hair-care products are, for example, shampoos for humans and animals, in particular dogs, hair conditioners, products for styling and treating hair, perming agents, hair sprays and lacquers, hair gels, hair fixatives and hair dyeing or bleaching agents.

Suitable dentifrices are in particular tooth creams, toothpastes, mouth-washes, mouth rinses, anti-plaque preparations and cleaning agents for dentures.

Suitable decorative preparations are in particular lipsticks, nail varnishes, eye shadows, mascaras, dry and moist make-up, rouge, powders, depilatory agents and suntan lotions.

Suitable cosmetic formulations containing active ingredients are in particular hormone preparations, vitamin preparations, vegetable extract preparations and antibacterial preparations.

The mentioned body-care products may be in the form of creams, ointments, pastes, foams, gels, lotions, powders, make-ups, sprays, sticks or aerosols.

They preferably contain the stabilizing mixture according to the present invention and, optionally, further UV absorbers, sterically hindered amines, complexing agents and phenolic or non-phenolic antioxidants.

The present invention therefore also relates to a body-care product comprising a stabilizing mixture according to the present invention.

In the stabilizing composition the weight ratio of component (a) to component (b) is from 20:1 to 1:20 and the weight ratio of component (a) to component (c) is from 1:1 to 1000:1, more preferably from 10:1 to 100:1.

The stabilizing mixture according to the present invention is present in the body care and household products in a concentration of about 5 to about 50000 ppm, based on the total formulation, preferably from about 10 to about 10000 ppm, and most preferably from about 100 to about 1000 ppm.

The body-care products according to the present invention may also contain one or one more additional compounds as described below.

Fatty Alcohols

Guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of $C_{12}$-$C_{15}$ alcohols, acetylated lanolin alcohol, etc.

Esters of Fatty Acids

Esters of linear $C_6$-$C_{24}$ fatty acids with linear $C_3$-$C_{24}$ alcohols, esters of branched $C_6$-$C_{13}$-carboxylic acids with linear $C_6$-$C_N$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols).

Examples of such ester oils are isopropylmyristate, isopropylpalmitate, isopropylstearate, isopropyl isostearate, isopropyloleate, n-butylstearate, n-hexyllaurate, n-decyloleate, iso-octylstearate, iso-nonylstearate, isononyl isononanoate, 2-ethylhexylpalmitate, 2-hexyllaurate, 2-hexyldecylstearate, 2-octyldodecylpalmitate, oleyloleate, oleylerucate, erucyloleate, erucylerucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Natural or Synthetic Triglycerides Including Glyceryl Esters and Derivatives

Di- or tri-glycerides, based on $C_6$-$C_{18}$ fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, borago oil, etc.

Waxes

Including esters of long-chain acids and alcohols as well as compounds having wax-like properties, e.g., carnauba wax, beeswax (white or yellow), lanolin wax, candellila wax, ozokerite, japan wax, paraffin wax, microcrystalline wax, ceresin, cetearyl esters wax, synthetic beeswax, etc. Also, hydrophilic waxes as Cetearyl Alcohol or partial glycerides.

Pearlescent Waxes

Alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils

Mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

Silicones or Siloxanes (Organosubstituted Polysiloxanes)

Dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form, linear polysiloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates.

A detailed survey by Todd et al. of suitable volatile silicones may in addition be found in Cosm. Toil. 91, 27 (1976).

Fluorinated or Perfluorinated Oils

Perfluorhexane, dimethylcyclohexane, ethylcyclopentane, polyperfluoromethylisopropyl ether.

Emulsifiers

Any conventionally usable emulsifier can be used for the compositions. Emulsifier systems may comprise for example: carbocyclic acids and their salts: alkaline soap of sodium, potassium and ammonium, metallic soap of calcium or magnesium, organic basis soap such as Lauric, palmitic, stearic and oleic acid etc., alkyl phosphates or phosphoric acid esters, acid phosphate, diethanolamine phosphate, potassium cetyl phosphate, ethoxylated carboxylic acids or polyethyleneglycol esters, PEG-n acrylates, linear fatty alcohols having from 8 to 22 carbon atoms, branched from 2 to 30 mol of ethylene oxide and/or from 0 to 5 mol propylene oxide with fatty acids having from 12 to 22 carbon atoms and with alkyl-phenols having from 8 to 15 carbon atoms in the alkyl group, fatty alcohol polyglycolether such as laureth-n, ceteareth-n, steareth-n, oleth-n, fatty acid polyglycolether such as PEG-n stearate, PEG-n oleate, PEG-n cocoate. Monoglycerides and polyol esters. $C_{12}$-$C_{22}$ fatty acid mono- and di-esters of addition products of from 1 to 30 mol of ethylene oxide with polyols.

Fatty acid and polyglycerol ester such as monostearate glycerol, diisostearoyl polyglyceryl-3-diisostearates, polyglyceryl-3-diisostearates, triglyceryl diisostearates, polyglyceryl-2-sesqui-isostearates or polyglyceryl dimerates (mixtures of compounds from a plurality of those substance classes are also suitable); fatty acid polyglycolesters such as monostearate diethylene glycol, fatty acid and polyethylene glycol esters, fatty acid and saccharose esters such as sucro esters, glycerol and saccharose esters such as sucro glycerides, sorbitol and sorbitan, sorbitan mono- and di-esters of saturated and unsaturated fatty acids having from 6 to 22 carbon atoms and ethylene oxide addition products, polysorbate-n series, sorbitan esters such as sesquiisostearate, sorbitan, PEG-(6)-isostearate sorbitan, PEG-(10)-sorbitan laurate, PEG-17-dioleate sorbitan, glucose derivatives, $C_8$-$C_{22}$ alkyl-mono and oligo-glycosides and ethoxylated analogues with glucose being preferred as the sugar component, 0/W emulsifiers such as methyl gluceth-20 sesquistearate, sorbitan stearate/sucrose cocoate, methyl glucose sesquistearate, cetearyl alcohol/cetearyl glucoside, W/O emulsifiers such as methyl glucose dioleate/methyl glucose isostearate, sulfates and sulfonated derivatives, dialkylsulfosuccinates, dioctyl succinate, alkyl lauryl sulfonate, linear sulfonated parafins, sulfonated tetraproplyne sulfonate, sodium lauryl sulfates, amonium and ethanolamine lauryl sulfates, lauyl ether sulfates, sodium laureth sulfates, sulfosuccinates, aceyl isothionates, alkanolamide sulfates, taurines, methyl taurines, imidazole sulfates, amine derivatives, amine salts, ethoxylated amines, oxide amine with chains containing an heterocycle such as alkyl imidazolines, pyridine derivatives, isoquinoteines, cetyl pyridinium chlorure, cetyl pyridinium bromide, quaternary ammonium such as cetyltrimethylbroide amonium broide (CTBA), stearylalkonium, amide derivatives, alkanolamides such as acylamide DEA, ethoxylated amides such as PEG-n acylamide, oxydeamide, polysiloxane/polyalkyl/polyether copolymers and derivatives, dimethicone, copolyols, silicone polyethylene oxide copolymer, silicone glycol copolymer, propoxylated or POE-n ethers (Meroxapols), polaxamers or poly(oxyethylene)m-block-poly(oxypropylene)n-block(oxyethylene), zwitterionic surfactants that carry at least one quaternary ammonium group and at least one carboxylate and/or sulfonate group in the molecule, zwitterionic surfactants that are especially suitable are betaines, such as N-alkyl-N,N dimethylammonium glycinates, cocoalkyldimethylammonium glycinate, N-acylaminopropyl-N,N-dimethylammonium glycinates, cocoacylaminopropyldimethylammonium glycinate and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate, N-alkylbetaine, N-alkylaminobetaines, alkylimidazolines, alkylopeptides, lipoaminoacides, self emulsifying bases and the compounds as described in K. F. DePolo, A short textbook of cosmetology, Chapter 8, Table 8-7, p 250-251.

Non ionic emulsifiers such as PEG-6 beeswax (and) PEG-6 stearate (and) polyglyceryl-2-isostearate [Apifac], glyceryl stearate (and) PEG-100 stearate. [Arlacel 165], PEG-5 glyceryl stearate [arlatone 983 S], sorbitan oleate (and) polyglyceryl-3 ricinoleate. [Arlacel 1689], sorbitan stearate and sucrose cocoate [arlatone 2121], glyceryl stearate and laureth-23 [Cerasynth 945], cetearyl alcohol and ceteth-20 [Cetomacrogol Wax], cetearyl alcohol and colysorbate 60 and PEG-150 and stearate-20 [Polawax GP 200, Polawax NF], cetearyl alcohol and cetearyl polyglucoside [Emulgade PL 1618], cetearyl alcohol and ceteareth-20 [Emulgade 1000NI, Cosmowax], cetearyl alcohol and PEG-40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and szeareth-7 and steareth-10 [Emulsifying wax U.S.N.F], glyceryl stearate and PEG-75 stearate [Gelot 64], propylene glycol ceteth-3 acetate. [Hetester PCS], propylene glycol isoceth-3 acetate [Hetester PHA], cetearyl alcohol and ceteth-12 and oleth-12 [Lanbritol Wax N 21], PEG-6 stearate and PEG-32 stearate [Tefose 1500], PEG-6 stearate and ceteth-20 and steareth-20 [Tefose 2000], PEG-6 stearate and ceteth-20 and glyceryl stearate and steareth-20 [Tefose 2561], glyceryl stearate and ceteareth-20 [Teginacid H, C, X].

Anionic emulsifiers such as PEG-2 stearate SE, glyceryl stearate SE [Monelgine, Cutina KD], propylene glycol stearate [Tegin P], cetearyl Alcohol and Sodium cetearyl sulfate [Lanette N, Cutina LE, Crodacol GP], cetearyl alcohol and sodium lauryl sulfate [Lanette W], trilaneth-4 phopshate and glycol stearate and PEG-2 stearate [Sedefos 75], glyceryl stearate and sodium lauryl Sulfate [Teginacid Special]. Cationic acid bases such as cetearyl alcohol and cetrimonium bromide.

The emulsifiers may be used in an amount of, for example, from 1 to 30% by weight, especially from 4 to 20% by weight and preferably from 5 to 10% by weight, based on the total weight of the composition.

When formulated in O/W emulsions, the preferably amount of such emulsifier system could represent 5% to 20% of the oil phase.

Super-Fatting Agents

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Surfactants

Examples of suitable mild surfactants, that is to say surfactants especially well tolerated by the skin, include fatty alcohol polyglycol ether sulfates, monoglyceride sulfates, mono-and/or di-alkyl sulfosuccinates, fatty acid isethionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Consistency Regulators/Thickeners and Rheology Modifiers

Silicon dioxide, magnesium silicates, aluminium silicates, polysaccharides or derivatives thereof for example hyaluronic acid, xanthan gum, guar-guar, agar-agar, alginates, carraghenan, gellan, pectines, or modified cellulose such as hydroxycellulose, hydroxypropylmethylcellulose. In addition polyacrylates or homopolymer of reticulated acrylic acids and polyacrylamides, carbomer (carbopol types 980, 981, 1382, ETD 2001, ETD2020, Ultrez 10) or Salcare range such as Salcare SC80(steareth-10 alkyl ether/acrylates copolymer), Salcare SC81(acrylates copolymer), Salcare SC91 and Salcare AST (sodium acrylates copolymer/PPG-1 trideceth-6), sepigel 305(polyacrylamide/laureth-7), Simulgel NS and Simulgel EG (hydroxyethyl acrylate/sodium acryloyldimethyl taurate copolymer), Stabilen 30 (acrylates/vinyl isodecanoate crosspolymer), Pemulen TR-1 (acrylates/C10-30 alkyl acrylate crosspolymer), Luvigel EM (sodium acrylates copolymer), Aculyn 28 (acrylates/beheneth-25 methacrylate copolymer), etc.

Polymers

Suitable cationic polymers are, for example, cationic cellulose derivatives, for example a quaternised hydroxymethyl cellulose obtainable under the name Polymer JR 400 from Amerchol, cationic starches, copolymers of diallylammonium salts and acrylamides, quaternised vinylpyrrolidone/vinyl imidazole polymers, for example Luviquatâ (BASF), condensation products of polyglycols and amines, quaternised collagen polypeptides, for example lauryldimonion hydroxypropyl hydrolyzed collagen (LamequatâL/Grünau), quaternised wheat polypeptides, polyethyleneimine, cationic silicone polymers, for example amidomethicones, copolymers of adipic acid and dimethylaminohydroxypropyldiethylenetriamine (Cartaretin/Sandoz), copolymers of acrylic acid with dimethyldiallylammonium chloride (Merquat 550/Chemviron), polyaminopolyamides, as described, for example, in FR-A-2 252 840, and the crosslinked water-soluble polymers thereof, cationic chitin derivatives, for example of quaternised chitosan, optionally distributed as microcrystals; condensation products of dihaloalkyls, for example dibromobutane, with bisdialkylamines, for example bisdimethylamino-1,3-propane, cationic guar gum, for example Jaguar C-17, Jaguar C-16 from Celanese, quaternised ammonium salt polymers, for example Mirapol A-15, Mirapol AD-1, Mirapol AZ-1 from Miranol. As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethylammonium chloride/acrylate copolymers, octyl acrylamide/methyl methacrylatetert. butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatised cellulose ethers and silicones. Furthermore the polymers as described in EP 1093796 (pages 3-8, paragraphs 17-68) may be used.

Cationic Surfactants cetyl trimethyl ammonium bromide (CTAB), dimethicone copolyols, amidomethicones, acrylamidopropyltrimonium chloride/Acrylamide copolymer, guar hydroxypropyl trimonium chloride, hydroxycetyl hydroxyethyl dimonium chloride quaternium compounds as listed in International Cosmetic Ingredient Dictionary and Handbook, $7^{th}$ Edition 1997, for example Quaternium-80, polyquaternium compounds, as listed in International Cosmetic Ingredient Dictionary and Handbook, $7^{th}$ Edition 1997, for example polyquaternium-5, polyquaternium-6, polyquaternium-7, polyquaternium-10, polyquaternium-11, polyquaternium-17, polyquaternium-18, polyquaternium-24 or polyquaternium-27, polyquaternium-28, polyquaternium-32, polyquaternium-37.

Biogenic Active Ingredients

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorising Active Ingredients

As deodorising active ingredients are for example, antiperspirants, for example aluminium chlorohydrates (see J. Soc. Cosm. Chem. 24, 281 (1973)). Under the trade mark Locronâ of Hoechst AG, Frankfurt (FRG), there is available commercially, for example, an aluminium chlorohydrate corresponding to formula $Al_2(OH)5Cl \times 2.5H_2O$, the use of which is especially preferred (see J. Pharm. Pharmacol. 26, 531 (1975)). Besides the chlorohydrates, it is also possible to use aluminium hydroxyacetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen CAT, Henkel), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the germ flora and kill or inhibit the growth of sweat-decomposing bacteria can likewise be present in the preparations (especially in stick preparations). Examples include chitosan, phenoxyethanol and chlorhexidine gluconate. 5-chloro-2-(2,4-dichlorophenoxy)phenol (Triclosan, Irgasan, Ciba Specialty Chemicals Inc.) has also proved especially effective.

Anti-Dandruff Agents

As anti-dandruff agents there may be used, for example, climbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Hydrotropic Agents

For improvement of the flow behaviour it is also possible to employ hydrotropic agents, for example ethoxylated or non ethoxylated mono-alcohols, diols or polyols with a low number of carbon atoms or their ethers (e.g. ethanol, isopropanol, 1,2-dipropanediol, propyleneglycol, glyerin, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols for that purpose comprise preferably 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligo-glycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylolpropane, trimethyl-olbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives

Suitable preservatives include, for example methyl-, ethyl-, propyl-, butyl-parabens, benzalkonium chloride, 2-bromo-2-nitro-propane-1,3-diol, dehydroacetic acid, diazolidinyl urea, 2-dichloro-benzyl alcohol, dmdm hydantoin, formaldehyde solution, methyldibromoglutanitrile, phenoxyethanol, sodium hydroxymethylglycinate, imidazolidinyl urea, triclosan and further substance classes listed in the following reference: K. F. Depolo—A Short Textbook Of Cosmetology, Chapter 7, Table 7-2, 7-3, 7-4 And 7-5, P 210-219.

Bacteria-Inhibiting Agents

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

Perfume Oils

Mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

Other Adjuvants

It is furthermore possible for the cosmetic preparations to contain, as adjuvants, anti-foams, such as silicones, structurants, such as maleic acid, solubilisers, such as ethylene glycol, propylene glycol, glycerol or diethylene glycol, opacifiers, such as latex, styrene/PVP or styrene/acrylamide copolymers, propellants, such as propane/butane mixtures, N2O, dimethyl ether, CO2, N2 or air, so-called coupler and developer components as oxidation dye precursors, reducing agents, such as thioglycolic acid and derivatives thereof, thiolactic acid, cysteamine, thiomalic acid or mercaptoethanesulfonic acid, or oxidising agents, such as hydrogen peroxide, potassium bromate or sodium bromate.

Suitable insect repellents are, for example, N,N-diethyl-m-toluamide, 1,2-pentanediol or insect repellent 3535; suitable self-tanning agents are, for example, dihydroxyacetone and/or erythrulose or dihydroxy acetone and/or dihydroxy acetone precursors as described in WO 01/85124 and/or erythrulose.

The present stabilized compositions are particularly suitable for stabilizing body care products, in particular:

skin-care preparations, e.g. skin-washing and cleansing preparations in the form of tablet-form or liquid soaps, soapless detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils; body oils, body lotions, body gels; skin protection ointments;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances and odoriferous substances containing preparations (scents, eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile;

dentifrices, in particular tooth creams, toothpastes, mouthwashes, mouth rinses, anti-plaque preparations and cleaning agents for dentures;

decorative preparations, in particular lipsticks, nail varnishes, eye shadows, mascaras, dry and moist make-up, rouge, powders, depilatory agents and suntan lotions cosmetic formulations containing active ingredients, in particular hormone preparations, vitamin preparations, vegetable extract preparations and antibacterial preparations.

Suitable cosmetic formulations containing active ingredients are in particular hormone preparations, vitamin preparations, vegetable extract preparations and antibacterial preparations.

Presentation Forms

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a stick, in the form of a spray (spray with propellent gas or pump-action spray) or an aerosol, in the form of a foam, or in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition:
0.01 to 5% by weight of the stabilized composition of the present invention,
12.0% by weight of sodium laureth-2-sulfate,
4.0% by weight of cocamidopropyl betaine,
3.0% by weight of sodium chloride,
and water ad 100%.

For example, especially the following hair-cosmetic formulations may be used:

a1) spontaneously emulsifying stock formulation, comprising stabilized composition of the present invention, optionally another stabilizer, PEG-6-C10oxoalcohol and sorbitan sesquioleate, to which water and any desired quaternary ammonium compound, for example 4% minkamidopropyl dimethyl-2-hydroxyethylammonium chloride or Quaternium 80 is added;

a2) spontaneously emulsifying stock formulation comprising the stabilized composition of the present invention, optionally another stabilizer, tributyl citrate and PEG-20-sorbitan monooleate, to which water and any desired quaternary ammonium compound, for example 4% minkamidopropyl dimethyl-2-hydroxyethylammonium chloride or Quaternium 80 is added;

b) quat-doped solutions comprising the stabilized composition of the present invention in butyl triglycol and tributyl citrate; and optionally another stabilizer;

c) mixtures or solutions comprising the compound stabilized composition of the present invention with alkylpyrrolidone; and optionally another stabilizer.

Examples of body care products of the present invention are listed in the Table below:

| Body care product | Ingredients |
|---|---|
| Sun screen | Oils, emulsifers, water, UV absorbers, thickeners, antioxidants, stabilizer according to invention |
| moisturising cream | vegetable oil, emulsifier, thickener, perfume, water, antioxidant, stabilizer according to invention |
| Hair or body shampoo | surfactant, emulsifier, colorant, preservatives, perfume, antioxidant, stabilizer according to invention |
| Hair conditioner | surfactant, cationic polymers, emulsifier, colorant, preservatives, perfume, antioxidant, stabilizer according to invention |
| Toothpaste | cleaning agent, abbrasives, water, thickener, sweetener, flavor, colorant, antioxidant, stabilizer according to invention |
| lip-care stick | vegetable oil, wax, $TiO_2$, pigments, antioxidant, stabilizer according to invention |

Household Products

The stabilized compositions of the present invention are also used in household cleaning and treatment agents, for example in laundry products and fabric softeners, liquid cleansing and scouring agents, glass detergents, neutral cleaners (all-purpose cleaners), acid household cleaners (bath), bathroom cleaners, WC cleaners, for instance in washing, rinsing and dishwashing agents, kitchen and oven cleaners, clear rinsing agents, dishwasher detergents, shoe polishes, polishing waxes, floor detergents and polishes, metal, glass and ceramic cleaners, textile-care products, rug cleaners and carpet shampoos, agents for removing rust, color and stains (stain remover salt), furniture and multipurpose polishes and leather and vinyl dressing agents (leather and vinyl sprays) and air fresheners.

Household cleaning agents are aqueous or alcoholic (ethanol or isopropyl alcohol) solutions of one or more of the following components:

anionic, nonionic, amphoteric and/or cationic surfactants soaps, prepared by saponification of animal and vegetable greases organic acids, like hydrochloric acid, phosphoric acid, or sulfuric acid, for basic products inorganic (NaOH or KOH) or organic bases;

abrasives for improved cleaning of surfaces, waxes and/or silicones for maintenance and protection of surfaces, polyphosphates, substances which eliminate hypochlorite or halogens;

peroxides comprising bleaching activators like TAED, for example sodium perborate or $H_2O_2$;

enzymes;

in washing detergents discoloration inhibitors, soil-release compounds, grey scale inhibitors, foam inhibitors, fluorescent whitening agents;

cleaning agents based on wax may comprise solvents selected from benzine, turpentine and/or paraffines and emulsifiers based on wax;

filling agents like silicates, polyphosphates, Zeolithes for powdery cleaning agents;

pigments, lakes or soluble dyes;

perfumes; and light stabilizers, antioxidants and chelating agents.

Colored cleaning agents and decorative cosmetic products can comprise the following dyes:

- inorganic pigments, for example iron oxide (Iron Oxide Red, Iron Oxide Yellow, Iron Oxide Black, etc.), Ultramarines, Chromium Oxide Green or Carbon Black;
- natural or synthetic orgnic pigments;
- disperse dyes which may be solubilzed in solvents like direct hair dyes of the HC type, for example HC Red No. 3, HC Blue No. 2 and all other hair dyes listed in International Cosmetic Ingredient Dictionary and Handbook, 7th edition 19997) or the dispersion dyes listed in Color Index International or Society of Dyers and Colourists;
- color varnishes (insoluble salts of soluble dyes, like many Ca-, Ba- or Al-salts of anionic dyes);
- soluble anionic or cationic dyes, like acid dyes (anionic), basic dyes (cationic), direct dyes, reactive dyes or solvent dyes.

Generally, for the coloration of household- and body care products all substances are suitable which have an absorption in the visible light of electromagnetic radiation (wave length of ca. 4000 to 700 nm). The absorption is often caused by the following chromophores:

Azo- (mono-, di, tris-, or poly-)stilbene-, carotenoide-, diarylmethan-, triarylmethan-, xanthen-, acridin-, quinoline, methin- (also polymethin-), thiazol-, indamin-, indophenol-, azin-, oxazin, thiazin-, anthraquinone-, indigoid-, phtalocyanine- and further synthetic, natural and/or inorganic chromophores.

The present invention also relates to home care and fabric care products such as drain cleaners, disinfectant solutions, upholstery cleaners, automotive care products (e.g., to clean and/or polish and protect paint, tires, chrome, vinyl, leather, fabric, rubber, plastic and fabric), degreasers, polishes (glass, wood, leather, plastic, marble, granite, and tile, etc.), and metal polishes and cleaners. The present invention also relates to home care products such as candles, gel candles, air fresheners and fragrance oils (for the home).

Typical examples of household cleaning and treating agents are listed in the table below:

| Household cleaners/ household treating agents | Ingredients |
| --- | --- |
| detergent concentrate | surfactant mixture, builders, water, ethanol, pH adjuster, antioxidant, antioxidants, stabilizer according to invention |
| Cleaner | Surfactant mixture, water, pH adjuster, colorant, stabilizer according to invention |
| Bleaches | Hypochlorite or peroxide bleach, water, pH adjuster, EDTA, stabilizer according to invention |
| shoe polish wax | wax emulsifier, antioxidant, water, preservative, antioxidants, stabilizer according to invention |
| wax-containing floor cleaning agent | emulsifier, wax, sodium chloride, water, preservative, antioxidant, stabilizer according to invention |

Colored cleaning agents, personal care and decorative cosmetic products can comprise the following dyes and pigments:

- inorganic pigments, for example iron oxide (Iron Oxide Red, Iron Oxide Yellow, Iron Oxide Black, etc.), Ultramarines, Chromium Oxide Green or Carbon Black;
- natural or synthetic organic pigments;
- dispersed dyes which may be solubilzed in solvents like direct hair dyes of the HC type, for example HC Red No. 3, HC Blue No. 2 and all other hair dyes listed in International Cosmetic Ingredient Dictionary and Handbook, 7th edition 19997) or listed in Color Index International or Society of Dyers and Colourists;
- color lakes (insoluble salts of soluble dyes, like many Ca-, Ba- or Al-salts of anionic dyes);
- soluble anionic or cationic dyes, like acid dyes (anionic), basic dyes (cationic), direct dyes, reactive dyes or solvent dyes.

Generally, for the coloration of household- and body care products all substances are suitable which have an absorption in the visible light of electromagnetic radiation (wave length of ca. 4000 to 700 nm). The absorption is often caused by the following chromophores:

Azo- (mono-, di, tris-, or poly-)stilbene-, carotenoide-, diarylmethan-, triarylmethan-, xanthen-, acridin-, quinoline, methin- (also polymethin-), thiazol-, indamin-, indophenol-, azin-, oxazin, thiazin-, anthraquinone-, indigoid-, phtalocyanine- and further synthetic, natural and/or inorganic chromophores.

The stabilized composition of the present invention are for example incorporated by dissolution in an oil phase or alcoholic or water phase, where required at elevated temperature.

The present body care products and household products have high stability towards color changes and chemical degradation of the ingredients present in these products. For example, present compositions that comprise a dye are found to have excellent color stability.

The following Examples illustrate the invention.

A. PREPARATION EXAMPLES

Example A1

Preparation of Merocyanine of Formula (MC-01)

40.13 g dimethylsulfate is added dropwise to 75.43 g 3-[(2-ethylhexyl)amino]-5,5-dimethyl-2-cyclohexen-1-one (CAS: 110186-59-9).

The mixture is heated under stirring for 40 min at 90-100° C.

After cooling down the reaction mixture to 60° C. first 31.33 g methyl cyanoacetate and then subsequently 33.21 g triethylamine are added.

The resulting mixture is then stirred at 100-110° C. for about 70 min.

After cooling to room temperature the mixture is diluted with 240 ml toluene.

The toluene solution is washed with 240 ml water and then extracted with 120 ml of an aqueous HCl solution (5%) and 3-times with 120 ml of water.

The organic phase is then washed with 120 ml aqueous NaOH solution (5%) and three times with 120 ml water.

The organic phase is then filtered over a silica gel pad and eluted with 5l toluene in total.

After distilling off the solvent 76 g of the product is obtained as an orange oil.

The product can be dissolved in methanol and precipitated by the addition of water yielding yellowish crystals (melting point: 78-81° C.).

B. APPLICATION EXAMPLES

Example B1

The following colored basic shampoo formulation was prepared:

| | |
|---|---|
| Sodium Laureth Ether Sulfate | 10 (w/w) % |
| Cocamidopropylbetaine | 3 (w/w) % |
| Citric Acid | to pH 5 |
| FD&C Blue No. 1 | 0.001 (w/w) % |
| Aqua | ad. 100 (w/w) % |
| Stabilizer | q.a. |

The following stabilized and unstabilized samples of this formulation are prepared for light stability testing:
(1) unstabilized basic shampoo formulation
(2) basic shampoo formulation plus 0.03% of the compound (BT-01)
(3) basic shampoo formulation plus 0.003% of compound (MC-03)
(4) basic shampoo formulation plus 0.003% of compound (MC-03) and 0.027% of the compound (BT-01)
(5) basic shampoo formulation plus 0.0075% of compound (MC-03) and 0.0225% of the compound (BT-01) (corresponds to 0.03% of a 1:3 (w %)-mixture of compound (MC-03) and of the compound (BT-01)).

The formulations are filled into 30 ml glass bottles and irradiated in an ATLAS Suntest XLS+ Xenon Lamp (light intensity 500 W/m2, spectrum of light adjusted to indoor conditions, sample chamber temperature: 32° C.).
Results:

| Sample | Irradiation Time until samples were significantly faded |
|---|---|
| (1) | 2 hours (colorless) |
| (2) | 8 hours (colorless) |
| (3) | 6 hours (faded, but still colored), 8 hours (colorless) |
| (4) | 18 hours (colorless) |
| (5) | 24 hours (colorless) |

Samples (4) and (5), stabilized by the synergistic combination of the compound (BT-01) with (MC-03), exhibit significantly better light stability compared to the samples when the compound (BT-01) (Sample (2)) or the merocyanine UV filter (MC-03) (Sample (3)) are used alone.

Sample (2), stabilized with 0.03% of the compound (BT-01), is totally faded after 8 hours.

In Sample (5), where 25% of the compound (BT-01) are replaced by the merocyanine (MC-03), the fading time is more than doubled to 18 hours.

Example B2

The following colored basic shampoo formulation is prepared:

| | |
|---|---|
| Texapon NSO | 30 (w/w) % |
| Dehyton K | 10 (w/w) % |
| Aqua | 60 (w/w) % |
| Citric Acid | to pH 5 |
| PURICOLOR Blue ABL9 | 0.001 (w/w) % |
| Aqua | ad. 100 (w/w) % |
| Stabilizer | q.a. |

The following stabilized and unstabilized samples of this formulation were prepared for light stability testing:
(6) unstabilized basic shampoo formulation
(7) basic shampoo formulation plus 0.03% of the compound (BT-01);
(8) basic shampoo formulation plus 0.02% of the compound (BT-01) and 0.01% of the compound (ESS-01);
(9) basic shampoo formulation plus 0.03% of a 1:3 (w %)-mixture of compound (MC-03) and of the compound (BT-01);
(10) basic shampoo formulation plus 0.03% of a 1:4 (w %)-mixture of compound (MC-03) and of the compound (BT-01);
(11) basic shampoo formulation plus 0.02% of a 1:3 (w %)-mixture of compound (MC-03) and of the compound (BT-01) plus additional 0.01% of the compound (ESS-01);
(12) basic shampoo formulation plus 0.02% of a 1:4 (w %)-mixture of compound (MC-03) and of the compound (BT-01) plus additional 0.01% of the compound (ESS-01).

The formulations are filled into 30 ml glass bottles and irradiated in an ATLAS Suntest XLS+ Xenon Lamp (light intensity 500 W/m2, spectrum of light adjusted to indoor conditions, sample chamber temperature: 32° C.).

| Results | |
|---|---|
| Sample | Irradiation Time until samples were significantly faded |
| (6) | 9 hours (nearly colorless) |
| (7) | 9 hours (faded), 24 hours (colorless) |
| (8) | 39 hours (strongly faded, but still colored) |
| (9) | 31 hours (faded, but still colored) |
| (10) | 31 hours (faded, but still colored) |
| (11) | 63 hours (still no fading observed) |
| (12) | 63 hours (still no fading observed) |

Samples 9 and 10, stabilized by the synergistic combination of the compound (BT-01) with (MC-03), exhibited significantly better light stability compared to the samples when the compound (BT-01) (Sample (7)) is used alone.

Best performance is shown by a combination of the compound (BT-01) and (MC-03) with the compound (ESS-01). Even after 63 hours of irradiation no fading is observed in the samples (11) and (12).

Example B3-B17

Preparation of Body-Care and Household Formulations

| Example B3: Preparation of a sprayable hair styling gel: | | |
|---|---|---|
| Phase | Ingredients | (w/w) % |
| A | carbomer (1% dispersion) | 0.30 |
| | water, demin. | 30.00 |
| B | glycerol | 2.00 |
| | methylparaben | 0.20 |
| C | water, demin. | ad 100 |
| | PVP/VA copolymer | 8.00 |
| | triethanolamine (88%) | 0.12 |
| | EDTA, disodium salt | 0.01 |
| | (BT-01) (INCI Benzotriazolyl Dodecyl p-Cresol) | 0.08 |
| | Merocyanine (MC-01) | 0.02 |

Preparation:
The components (A) are dispersed at room temperature. (B) is mixed under heating until the paraben is completely dissolved and then (B) is added with gentle stirring to (A). (C) is blended until it is completely dissolved and is slowly added under stirring to the mixture of (A) and (B).

The transparency of the gel can be increased by adding small amounts of triethanolamine (pH=5.6-5.75).

Example B4: Preparation of a baby shampoo

| Ingredients | (w/w) % |
|---|---|
| cocoamidopropylbetaine | 35.00 |
| water, demin. | ad.100 |
| citric acid | q.s. (pH) |
| polyquaternium-15 | 0.15 |
| perfume oil | 0.30 |
| chlorophyll | 0.20 |
| Merocyanine (MC-03) | 0.02 |
| Compound (BT-01) (INCI Benzotriazolyl Dodecyl p-Cresol) | 0.02 |
| colorant (D&C Yellow No. 5) | 0.02 |
| sodium chloride | 0.30 |

Preparation:

Surfactant and water are blended until a homogeneous solution is obtained. The pH is adjusted to 6.0-6.5 with citric acid and the other components are added in the indicated sequence. The mixture is stirred until it is completely dissolved.

Example B5: Preparation of a perfumed toilet water

| Ingredients | (w/w) % |
|---|---|
| ethanol, 96% | 60 |
| d-limonene | 5 |
| cedrene | 1.5 |
| citronellol | 0.5 |
| savin | 0.5 |
| Merocyanine (MC-03) | 0.05 |
| Compound (BT-01) (INCI Benzotriazolyl Dodecyl p-Cresol) | 0.05 |
| Compound (ESS-01) (INCI: Tris (tetramethylhydroxypiperidinol) citrate) | 0.03 |
| Tinogard TS (CAS number: 2082-79-3) | 0.02 |
| S,S-EDDS | 0.01 |
| colorant (D&C Yellow No. 5) | 0.1 |
| water | ad. 100 |

Preparation:

The components are thoroughly mixed in the indicated sequence at 50° C. A clear homogeneous solution is obtained.

Preparation of Formulations of Household Products

Example B6: Preparation of a green-colored glass detergent

| Ingredients | (w/w) % |
|---|---|
| anionic/amphoteric surfactants (Lumorol RK) | 0.7 |
| butyl glycol | 5.0 |
| isopropanol | 20.0 |
| d-limonene | 4.00 |
| colorant (D&C Green No. 2) | 0.05 |
| Compound (ESS-01) (INCI: Tris (tetramethylhydroxypiperidinol) citrate) | 0.05 |
| Merocyanine (MC-01) | 0.01 |
| Compound (BT-01) (INCI Benzotriazolyl Dodecyl p-Cresol) | 0.03 |
| water, demin. | ad. 100 |

Preparation:

The components are dissolved in the indicated sequence until a clear homogeneous mixture is obtained.

Example B7: Preparation of a floor wax

| Ingredients | (w/w) % |
|---|---|
| wax mixture | 12 |
| white spirit | ad 100 |
| d-limonene | 4.00 |
| Merocyanine (MC-03) | 0.025 |
| Compound (BT-01) (INCI Benzotriazolyl Dodecyl p-Cresol) | 0.075 |

Preparation:

The components are stirred in the indicated sequence until a homogeneous mixture is obtained.

Example B8: Preparation of a lipstick, non-greasy

| Ingredients | (w/w) % |
|---|---|
| Carnauba wax | 2.5 |
| Beeswax, white | 20.0 |
| Ozekerite | 10.0 |
| Lanoline, anhydrous | 5.0 |
| Cetyl alcohol | 2.0 |
| Liquid paraffin | 3.0 |
| Isopropyl Myristate | 3.0 |
| Propylene glycol recinoleate | 4.0 |
| CI Pigment Red 4 | 9.0 |
| CI Pigment Blue 15 | 1.0 |
| Merocyanine (MC-03) | 0.025 |
| Compound (BT-01) (INCI Benzotriazolyl Dodecyl p-Cresol) | 0.075 |
| Castor Oil | ad 100 |

Example B9: Preparation of a lipstick, transfer resistant

| Ingredients | (w/w) % |
|---|---|
| Cyclomethicone | 41.50 |
| Isodecane | 10.00 |
| D&C Red No. 7 | 8.00 |
| Synthetic wax | 6.00 |
| Isostearyltrimethylpropane siloxysilicate | 5.00 |
| Cetylstearate/acetylated lanolin, 90:10 | 5.00 |
| Ceresin | 4.00 |
| Paraffin | 3.00 |
| Titanium dioxide | 2.00 |
| Methylparaben | 0.30 |
| Propylparaben | 0.10 |
| Tinogard AS (INCI Bumetrizole) | 0.10 |
| Merocyanine (MC-03) | 0.02 |
| Compound (BT-01) (INCI Benzotriazolyl Dodecyl p-Cresol) | 0.08 |

Example B10: Preparation of a Rouge (powder)

| Ingredients | (w/w) % |
|---|---|
| Talcum | 56 |
| Zinc Stearate | 15 |
| Rice starch | 15 |
| Iron Oxide Red | 12 |
| Perfume | q.s. |
| Merocyanine (MC-03) | 0.02 |
| Compound (BT-01) (INCI Benzotriazolyl Dodecyl p-Cresol) | 0.08 |

Example B11: Preparation of a Foundation cream

| Ingredients | (w/w) % |
|---|---|
| Titanium dioxide | 12.79 |
| Oleyl alcohol | 4.57 |
| Glyceryl stearate | 3.65 |
| Propylene glycol | 3.65 |
| Stearic acid | 1.83 |
| Magnesium aluminium silicate | 0.91 |
| Triethanolamine 99% | 0.91 |
| Iron Oxide Yellow | 0.64 |
| Iron Oxide Red | 0.32 |
| CI Pigment Brown 6 | 0.37 |
| Carboxymethyl cellulose | 0.10 |
| Merocyanine (MC-03) | 0.025 |
| Compound (BT-01) (INCI Benzotriazolyl Dodecyl p-Cresol) | 0.075 |
| Water | ad 100 |

Example B12: Preparation of an Eyeliner

| Ingredients | (w/w) % |
|---|---|
| Polysaccharide resin (Kama KM 13, Kama) | 8 |
| Iron Oxide Black | 6.50 |
| Carnauba wax | 1.00 |
| Triethanolamin, 99% | 1.00 |
| Hydrogenated polyisobutane | 1.00 |
| Hydrogenated polydecene | 1.00 |
| Sorbitan sesquioleate | 1.00 |
| Xanthum gum | 0.50 |
| Carboxymethyl cellulose | 0.40 |
| Magnesium aluminium silicate | 0.40 |
| Methyl paraben | 0.35 |
| Stearic acid | 2.50 |
| Lecithin | 0.20 |
| Imidazolidinyl urea | 0.10 |
| Merocyanine (MC-03) | 0.02 |
| Compound (BT-01) (INCI Benzotriazolyl Dodecyl p-Cresol) | 0.08 |
| Tinogard TT (INCI Pentaerythrityl Tetra-di-t-butyl hydroxyhydrocinnamate) | 0.05 |
| Water | to 100 |

Example B13: Preparation of an Eyelash Makeup

| Ingredients | (w/w) % |
|---|---|
| Paraffin Wax | 10.00 |
| Starch | 5.00 |
| Polyethylene | 5.00 |
| Iron Oxide Black | 7.00 |
| Carbomer (Carbopol, BFGoodrich) | 0.50 |
| Hydroxyethylcellulose | 0.50 |
| Panthenol | 2.00 |
| Merocyanine (MC-03) | 0.01 |
| Compound (BT-01) (INCI Benzotriazolyl Dodecyl p-Cresol) | 0.04 |
| Water | ad 100 |

Example B14: Preparation of a Nail Varnish

| Ingredients | (w/w) % |
|---|---|
| Poly(1-trimethylsilylpropylene) | 0.30 |
| Nitrocellulose | 12.00 |
| Alkyd resin | 10.00 |
| Dibutyl phthalate | 4.00 |
| Camphor | 2.00 |
| Butyl acetate | 49.50 |
| Toluene | 20.00 |
| Pigment Red 57.1 | 1.00 |
| Quaternary bentonite | 1.00 |
| Merocyanine (MC-03) | 0.06 |
| compound (BT-01) (INCI Benzotriazolyl Dodecyl p-Cresol) | 0.14 |
| Tinogard NOA (INCI Tetrabutyl Ethylidenebisphenol) | 0.10 |

Example B15: High Protection Sunscreen

| High protection sunscreen (1) INCI-Name | A % w/w | B % w/w | C % w/w | D % w/w |
|---|---|---|---|---|
| Synthetic Beeswax | 0.5 | 0.5 | 0.5 | 0.5 |
| Ethylhexyl Methoxycinnamate | 9.8 | 9.8 | 9.8 | 9.8 |
| Isoamyl p-Methoxycinnamate | 2.0 | 2.0 | 2.0 | 2.0 |
| Ethylhexyl Salicylate | 5.0 | 5.0 | 5.0 | 5.0 |
| Butyl Methoxydibenzoylmethane | 4.0 | 4.0 | 4.0 | 4.0 |
| 4-Methylbenzylidene Camphor | 4.0 | 4.0 | 4.0 | 4.0 |
| Bis-Ethylhexyloxyphenol Methoxyphenyl Triazine | 2.0 | 3.0 | 2.0 | 1.0 |
| Octadecene/MA Copolymer (and) Methyl Acetyl Ricinoleate (and) Di-methylhepthyl Adipate | | 3.0 | | |
| C30-38 olefin/isopropyl maleate/MA copolymer | | | 2.0 | |
| Hydrogenated Dimer Dilinoleyl/Dimethylcarbonate Copolymer | | | | 3.0 |
| Dimethicone | 4.5 | 4.5 | 4.5 | 4.5 |
| C20-22 Alkyl Phosphate (and) C20-22 Alcohols | | 3.0 | | |
| Candelilla/Jojoba/Rice Bran Polyglyceryl-3 esters (and) glyceryl stearate (and) Cetearyl alcohol (and) Sodium stearoyl lactylate | | | 4.0 | |
| Glyceryl oleate citrate (and) Caprylic/Capric Triglycerides | | | | 6.0 |
| Cetearyl Alcohol (and) Dicetyl Phosphate (and) Ceteth-10 Phosphate | 4.5 | | | |
| Cetyl Ricinoleate | 3.0 | 3.0 | 3.0 | 3.0 |

Example B15: High Protection Sunscreen

| | | | | |
|---|---|---|---|---|
| Pentaerythrityl Distearate | | 1.5 | | |
| Glyceryl Dibehenate (and) Tribehenin (and) Glyceryl Behenein | | | 2.0 | |
| Hydroxypropyl Dimethicone Behenate | 2.2 | 1.0 | | 2.2 |
| Decyl Cocoate | 1.0 | 1.0 | 1.0 | 1.0 |
| Aqua | Qs to 100 | Qs to 100 | Qs to 100 | Qs to 100 |
| Propylene Glycol | 3.0 | 3.0 | 3.0 | 3.0 |
| Methylene Bis-Benzotriazolyl Tetramethylbutylphenol (and) Aqua (and) Decyl Glucoside (and) Propylene Glycol (and) Xanthan Gum | 5.0 | 4.0 | 6.0 | 8.0 |
| Decyl Glucoside | 0.5 | 0.5 | 0.5 | 0.5 |
| Acrylates/Vinyl Neodecanoate Crosspolymer | | | | |
| Ammonium Acryloyldimethyltaurate/VP Copolymer | 0.3 | 0.3 | 0.3 | 0.3 |
| Phenylbenzimidazole Sulfonic Acid | 2.0 | 2.0 | 2.0 | 2.0 |
| Disteareth-75 IPDI | | 0.3 | 3.0 | |
| Disteareth-100 IPDI | | | | 0.3 |
| Acrylates/C10-30 Alkyl Acrylate Crosspolymer | 0.2 | | | |
| Disodium EDTA | 0.2 | 0.2 | 0.2 | 0.2 |
| Tromethamine | 0.8 | 0.8 | 0.8 | 0.8 |
| Cyclohexasiloxane (and) Cyclopentasiloxane | 0.8 | 0.8 | 0.8 | 0.8 |
| Phenoxyethanol (and) Methylparaben (and) Ethylparaben (and) Butylparaben (and) Propylparaben (and) Isobutylparaben | 0.8 | 0.8 | 0.8 | 0.8 |
| Tocopheryl Acetate | 0.4 | 0.4 | 0.4 | 0.4 |
| CAS-Regno. 88122-99-0, Ethylhexyl triazone (Octyl triazone; Uvinul T 150) | 2.0 | 1.5 | 2.0 | |
| CAS-Regno. 6197-30-4, Octocrylene | 3.0 | 4.0 | 5.0 | |
| CAS-Regno. 180898-37-7, Disodium phenyldibenzimidazoletetrasulfonate Neo Heliopan AP or Neo-Heliopan APC | 3.0 | 4.0 | 5.0 | 3.0 |
| CAS-Regno. 302776-68-7, Uvinul A Plus | 4.0 | | 5.0 | |
| CAS-Regno. 444811-29-4, Propanedioic acid. [(4-hydroxy-3,5-dimethoxyphenyl)methylene]-, bis(2-ethylhexyl) ester (Oxynex ST) | 3.0 | | 1.0 | |
| CAS-Regno. 477844-93-2, Octofluorene | | 3.0 | 1.0 | |
| 2-phenylethylbenzoate | | 1.0 | 1.0 | |
| CAS-Regno. 68890-66-4, Octopirox | 2.0 | | | 3.0 |
| Tinogard TT (INCI Tetradibutyl Pentaerithrityl Hydroxy-hydrocinnamate) | 1.0 | | 1.0 | 1.0 |
| Tinogard HS (INCI Sodium Benzotriazolyl Butylphenol Sulfonate) | | 2.0 | 3.0 | |
| compound (BT-01) (INCI Benzotriazolyl Dodecyl p-Cresol) | 2.0 | 0.9 | 1.0 | 1.0 |
| Merocyanine (MC-03) | 1.0 | 0.9 | 0.3 | 0.3 |
| Cibafast H Liquid (INCI Sodium Benzotriazolyl Butylphenol Sulfonate, Buteth-3, Tributyl Citrate) | 1.0 | | | |
| Tinogard AS (INCI Bumetrizole) | 2.0 | | 1.0 | |
| Tris(tetramethylhydroxypiperidinol) citrate of the Compound (ESS-01) | 1.0 | | 1.0 | |
| 220410-74-2 4-Piperidinol, 1-hydroxy-2,2,6,6-tetramethyl-, 2-hydroxy-1,2,3-propanetricarboxylate (3:1) (salt) | | | 1.0 | |
| CAS-Regno. 1750-49-8, N-(2-Hydroxypropyl)urea | | 5.0 | | |
| CAS-Regno. 2078-71-9, N-(2-Hydroxyethyl)urea | | | 10.0 | |
| mixture of n-butylphthalimide and isopropylphthalimide | 0.5 | | | 5.0 |

| High protection sunscreen (1) INCI-Name | E % w/w | F % w/w | G % w/w | H % w/w | I % w/w |
|---|---|---|---|---|---|
| Synthetic Beeswax | 0.5 | 0.5 | 0.5 | 0.5 | 0.5 |
| Ethylhexyl Methoxycinnamate | 9.8 | 9.8 | 9.8 | 9.8 | 9.8 |
| Isoamyl p-Methoxycinnamate | 2.0 | 2.0 | 2.0 | 2.0 | 2.0 |
| Ethylhexyl Salicylate | 5.0 | 5.0 | 5.0 | 5.0 | 5.0 |
| Butyl Methoxydibenzoylmethane | 4.0 | 4.0 | 3.0 | 4.0 | 3.0 |
| 4-Methylbenzylidene Camphor | 4.0 | 4.0 | 4.0 | 4.0 | 4.0 |
| Bis-Ethylhexyloxyphenol Methoxyphenyl Triazine | 1.0 | 1.0 | 1.0 | 1.0 | 1.0 |
| Cyclopentasiloxane (and) Acrylates/Polytrimethyl-siloxymethacrylate Copolymer | 7.0 | | | | |
| Isododecane (and) Acrylates/Polytrimethylsiloxy-methacrylate Copolymer | | 8.0 | | | |
| Poly(Glycol Adipate)/Bis-Hydroxyethyoxypropyl Dimethicone Copolymer | | | 5.0 | | |
| Dimethicone | 4.5 | 4.5 | 4.5 | 4.5 | 4.5 |
| C20-22 Alkyl Phosphate (and) C20-22 Alcohols | | 3.0 | | | |
| Candelilla/Jojoba/Rice Bran Polyglyceryl-3 esters (and) glyceryl stearate (and) Cetearyl alcohol (and) Sodium stearoyl lactylate | | | 4.0 | | |

| Example B15: High Protection Sunscreen | | | | | |
| --- | --- | --- | --- | --- | --- |
| Glyceryl oleate citrate (and) Caprylic/Capric Triglycerides | | | | 6.0 | |
| Cetearyl Alcohol (and) Dicetyl Phosphate (and) Ceteth-10 Phosphate | 4.5 | | | | 4.5 |
| Cetyl Ricinoleate | 3.0 | 3.0 | 3.0 | 3.0 | 3.0 |
| Pentaerythrityl Distearate | | | 3.0 | | 5.0 |
| Glyceryl Dibehenate (and) Tribehenin (and) Glyceryl Behenate | 4.0 | | | | |
| Hydroxypropyl Dimethicone Behenate | | 2.2 | 0.5 | 2.2 | |
| Decyl Cocoate | 1.0 | 1.0 | 1.0 | 1.0 | 1.0 |
| Aqua | Qs to 100 | Qs to 100 | Qs to 100 | Qs to 100 | Qs to 100 |
| Propylene Glycol | 3.0 | 3.0 | 3.0 | 3.0 | 3.0 |
| Methylene Bis-Benzotriazolyl Tetramethylbutyl-phenol (and) Aqua (and) Decyl Glucoside (and) Propylene Glycol (and) Xanthan Gum | 5.0 | 10.0 | 10.0 | 5.0 | 10.0 |
| Decyl Glucoside | 0.5 | 0.5 | 0.5 | 0.5 | 0.5 |
| Acrylates/Vinyl Neodecanoate Crosspolymer | | | | | |
| Ammonium Acryloyldimethyltaurate/VP Copolymer | 0.3 | 0.3 | 0.3 | 0.3 | 0.3 |
| PVP/dimethylconylacrylate/polycarbamyl/polyglycol ester | | | | | 10.0 |
| Polyester-5 | | | | 3.0 | |
| Phenylbenzimidazole Sulfonic Acid | 2.0 | 2.0 | 2.0 | 2.0 | 2.0 |
| Disteareth-75 IPDI | | | | | |
| Disteareth-100 IPDI | 3.0 | | | | |
| Acrylates/Vinyl Neodecanoate Crosspolymer | | 1.5 | 5.0 | 8.0 | |
| Acrylates/C10-30 Alkyl Acrylate Crosspolymer | | | | | 0.2 |
| Disodium EDTA | 0.2 | 0.2 | 0.2 | 0.2 | 0.2 |
| Tromethamine | 0.8 | 0.8 | 0.8 | 0.8 | 0.8 |
| Cyclohexasiloxane (and) Cyclopentasiloxane | 0.8 | 0.8 | 0.8 | 0.8 | 0.8 |
| Phenoxyethanol (and) Methylparaben (and) Ethyl-paraben (and) Butylparaben (and) Propylparaben (and) Isobutylparaben | 0.8 | 0.8 | 0.8 | 0.8 | 0.8 |
| Tocopheryl Acetate | 0.4 | 0.4 | 0.4 | 0.4 | 0.4 |
| CAS-Regno. 88122-99-0, Ethylhexyl triazone (Octyl triazone; Uvinul T 150) | 1.0 | | | 3.0 | |
| CAS-Regno. 6197-30-4, Octocrylene | | 1.0 | 5.0 | | |
| CAS-Regno. 180898-37-7, Disodium phenyldibenzimidazoletetrasulfonate Neo Heliopan AP or Neo-Heliopan APC | | | | | 2.0 |
| CAS-Regno. 68890-66-4, Octopirox | 1.0 | | | | |
| Tinogard TT (INCI Tetradibutyl Pentaerithrityl Hydroxy-hydrocinnamate) | 3.0 | | | | 1.0 |
| Tinogard HS (INCI Sodium Benzotriazolyl Butylphenol Sulfonate) | | 3.0 | | | |
| compound (BT-01) (INCI Benzotriazolyl Dodecyl p-Cresol) | 0.9 | 1.0 | 3.0 | 0.5 | 1.0 |
| Merocyanine (MC-03) | 0.3 | 1.0 | 1.0 | 0.5 | 0.3 |
| Cibafast H Liquid (INCI Sodium Benzotriazolyl Butylphenol Sulfonate, Buteth-3, Tributyl Citrate) | | | | | |
| Tinogard AS (INCI Bumetrizole) | | | | 1.0 | 1.0 |
| Tris(tetramethylhydroxypiperidinol) citrate of the Compound (ESS-01) | | | | 1.0 | 1.0 |
| 220410-74-2 4-Piperidinol, 1-hydroxy-2,2,6,6-tetramethyl-, 2-hydroxy-1,2,3-propanetricarboxylate (3:1) (salt) | | | | 1.0 | |
| CAS-Regno. 1750-49-8, N-(2-Hydroxypropyl)urea | | 10.0 | | | |
| CAS-Regno. 2078-71-9, N-(2-Hydroxyethyl)urea | 10.0 | | | | |
| mixture of n-butylphthalimide and isopropylphthalimide | | | | | 3.0 |

| Example B16: High Protection Sunscreen | | | | |
| --- | --- | --- | --- | --- |
| High protection sunscreen (2) INCI-Name | A % w/w | B % w/w | C % w/w | D % w/w |
| Synthetic Beeswax | 0.5 | 0.5 | 0.5 | 0.5 |
| Ethylhexyl Methoxycinnamate (stabilized by incorporating into a polymer) | 9.8 | 9.8 | 9.8 | 9.8 |
| Isoamyl p-Methoxycinnamate | 2.0 | 2.0 | 2.0 | 2.0 |
| Ethylhexyl Salicylate | 5.0 | 5.0 | 5.0 | 5.0 |
| Butyl Methoxydibenzoylmethane (stabilized by incorporating into a polymer) | 4.0 | 4.0 | 5.0 | 4.0 |
| 4-Methylbenzylidene Camphor | 4.0 | 4.0 | 4.0 | 4.0 |

| Example B16: High Protection Sunscreen | | | | |
|---|---|---|---|---|
| Bis-Ethylhexyloxyphenol Methoxyphenyl Triazine | 2.0 | 3.0 | 2.0 | 1.0 |
| Octadecene/MA Copolymer (and) Methyl Acethyl Ricinoleate (and) Di-methylhepthyl Adipate | | 3.0 | | |
| C30-38 olefin/isopropyl maleate/MA copolymer | | | 2.0 | |
| Hydrogenated Dimer Dilinoleyl/Dimethylcarbonate Copolymer | | | | 3.0 |
| Dimethicone | 4.5 | 4.5 | 4.5 | 4.5 |
| C20-22 Alkyl Phosphate (and) C20-22 Alcohols | | 3.0 | | |
| Candelilla/Jojoba/Rice Bran Polyglyceryl-3 esters (and) glyceryl stearate (and) Cetearyl alcohol (and) Sodium stearoyl lactylate | | | 4.0 | |
| Glyceryl oleate citrate (and) Caprylic/Capric Triglycerides | | | | 6.0 |
| Cetearyl Alcohol (and) Dicetyl Phosphate (and) Ceteth-10 Phosphate | 4.5 | | | |
| Cetyl Ricinoleate | 3.0 | 3.0 | 3.0 | 3.0 |
| Pentaerythrityl Distearate | | 1.5 | | |
| Glyceryl Dibehenate (and) Tribehenin (and) Glyceryl Behenate | | | 2.0 | |
| Hydroxypropyl Dimethicone Behenate | 2.2 | 1.0 | | 2.2 |
| Decyl Cocoate | 1.0 | 1.0 | 1.0 | 1.0 |
| Aqua | Qs to 100 | Qs to 100 | Qs to 100 | Qs to 100 |
| Propylene Glycol | 3.0 | 3.0 | 3.0 | 3.0 |
| Decyl Glucoside | 0.5 | 0.5 | 0.5 | 0.5 |
| Acrylates/Vinyl Neodecanoate Crosspolymer | | | | |
| Ammonium Acryloyldimethyltaurate/VP Copolymer | 0.3 | 0.3 | 0.3 | 0.3 |
| PVP/dimethylconylacrylate/polycarbamyl/polyglycol ester | | | | |
| Polyester-5 | | | | |
| Phenylbenzimidazole Sulfonic Acid | 2.0 | 2.0 | 2.0 | 2.0 |
| Disteareth-75 IPDI | | 0.3 | 3.0 | |
| Disteareth-100 IPDI | | | | 0.3 |
| Acrylates/C10-30 Alkyl Acrylate Crosspolymer | 0.2 | | | |
| Disodium EDTA | 0.2 | 0.2 | 0.2 | 0.2 |
| Methylene Bis-Benzotriazolyl Tetramethylbutylphenol | 5.0 | 5.0 | 5.0 | 5.0 |
| Tromethamine | 0.8 | 0.8 | 0.8 | 0.8 |
| Cyclohexasiloxane (and) Cyclopentasiloxane | 0.8 | 0.8 | 0.8 | 0.8 |
| Phenoxyethanol (and) Methylparaben (and) Ethylparaben (and) Butylparaben (and) Propylparaben (and) Isobutylparaben | 0.8 | 0.8 | 0.8 | 0.8 |
| Tocopheryl Acetate | 0.4 | 0.4 | 0.4 | 0.4 |
| CAS-Regno. 88122-99-0, Ethylhexyl triazone (Octyl triazone; Uvinul T 150) | 2.0 | 1.5 | 2.0 | |
| CAS-Regno. 6197-30-4, Octocrylene | 3.0 | 4.0 | 5.0 | |
| CAS-Regno. 180898-37-7, Disodium phenyldibenzimidazoletetrasulfonate Neo Heliopan AP or Neo-Heliopan APC | 3.0 | 4.0 | 5.0 | 3.0 |
| CAS-Regno. 302776-68-7, Uvinul A Plus | 4.0 | | 5.0 | |
| CAS-Regno. 444811-29-4, Propanedioic acid, [(4-hydroxy-3,5-dimethoxyphenyl)methylene]-, bis(2-ethylhexyl) ester (Oxynex ST) | 3.0 | | 1.0 | |
| CAS-Regno. 477844-93-2, Octofluorene | | 3.0 | 1.0 | |
| 2-phenylethylbenzoate | | 1.0 | 1.0 | |
| CAS-Regno. 68890-66-4, Octopirox | 2.0 | | | 3.0 |
| Tinogard TT (INCI Tetradibutyl Pentaerithrityl Hydroxy-hydrocinnamate) | 1.0 | | 1.0 | 1.0 |
| Tinogard HS (INCI Sodium Benzotriazolyl Butylphenol Sulfonate) | | 2.0 | 3.0 | |
| compound (BT-01) (INCI Benzotriazolyl Dodecyl p-Cresol) | 2.0 | 1.0 | 1.0 | 1.0 |
| Merocyanine (MC-03) | 2.0 | 2.0 | 1.0 | 1.0 |
| Cibafast H Liquid (INCI Sodium Benzotriazolyl Butylphenol Sulfonate, Buteth-3, Tributyl Citrate) | 1.0 | | | |
| Tinogard AS (INCI Bumetrizole) | 2.0 | | 1.0 | |
| Tris(tetramethylhydroxypiperidinol) citrate Compound (ESS-01) | 1.0 | | 1.0 | |
| 220410-74-2 4-Piperidinol, 1-hydroxy-2,2,6,6-tetramethyl-, 2-hydroxy-1,2,3-propanetricarboxylate (3:1) (salt) | | | 1.0 | |
| CAS-Regno. 1750-49-8, N-(2-Hydroxypropyl)urea | | 5.0 | | |
| CAS-Regno. 2078-71-9, N-(2-Hydroxyethyl)urea | | | 10.0 | |
| mixture of n-butylphthalimide and isopropylphthalimide | 0.5 | | | 5.0 |

| Example B16: High Protection Sunscreen | | | | | |
|---|---|---|---|---|---|
| High protection sunscreen (2)<br>INCI-Name | E<br>% w/w | F<br>% w/w | G<br>% w/w | H<br>% w/w | I<br>% w/w |
| Synthetic Beeswax | 0.5 | 0.5 | 0.5 | 0.5 | 0.5 |
| Ethylhexyl Methoxycinnamate (stabilized by incorporating into a polymer) | 9.8 | 9.8 | 9.8 | 9.8 | 9.8 |
| Isoamyl p-Methoxycinnamate | 2.0 | 2.0 | 2.0 | 2.0 | 2.0 |
| Ethylhexyl Salicylate | 5.0 | 5.0 | 5.0 | 5.0 | 5.0 |
| Butyl Methoxydibenzoylmethane (stabilized by incorporating into a polymer) | 4.0 | 4.0 | 3.0 | 5.0 | 3.0 |
| 4-Methylbenzylidene Camphor | 4.0 | 4.0 | 4.0 | 4.0 | 4.0 |
| Bis-Ethylhexyloxyphenol Methoxyphenyl Triazine | 1.0 | 1.0 | 1.0 | 1.0 | 1.0 |
| Cyclopentasiloxane (and) Acrylates/Polytrimethylsiloxymethacrylate Copolymer | 7.0 | | | | |
| Isododecane (and) Acrylates/Polytrimethylsiloxymethacrylate Copolymer | | 8.0 | | | |
| Poly(Glycol Adipate)/Bis-Hydroxyethyoxypropyl Dimethicone Copolymer | | | 5.0 | | |
| Dimethicone | 4.5 | | 4.5 | 4.5 | 4.5 |
| C20-22 Alkyl Phosphate (and) C20-22 Alcohols | | 3.0 | | | |
| Candelilla/Jojoba/Rice Bran Polyglyceryl-3 esters (and) glyceryl stearate (and) Cetearyl alcohol (and) Sodium stearoyl lactylate | | | 4.0 | | |
| Glyceryl oleate citrate (and) Caprylic/Capric Triglycerides | | | | 6.0 | |
| Cetearyl Alcohol (and) Dicetyl Phosphate (and) Ceteth-10 Phosphate | 4.5 | | | | 4.5 |
| Cetyl Ricinoleate | 3.0 | 3.0 | 3.0 | 3.0 | 3.0 |
| Pentaerythrityl Distearate | | | 3.0 | | 5.0 |
| Glyceryl Dibehenate (and) Tribehenin (and) Glyceryl Behenate | 4.0 | | | | |
| Hydroxypropyl Dimethicone Behenate | | 2.2 | 0.5 | 2.2 | |
| Decyl Cocoate | 1.0 | 1.0 | 1.0 | 1.0 | 1.0 |
| Aqua | Qs to 100 | Qs to 100 | Qs to 100 | Qs to 100 | Qs to 100 |
| Propylene Glycol | 3.0 | 3.0 | 3.0 | 3.0 | 3.0 |
| Decyl Glucoside | 0.5 | 0.5 | 0.5 | 0.5 | 0.5 |
| Acrylates/Vinyl Neodecanoate Crosspolymer | | | | | |
| Ammonium Acryloyldimethyltaurate/VP Copolymer | 0.3 | 0.3 | 0.3 | 0.3 | 0.3 |
| PVP/dimethylconylacrylate/polycarbamyl/polyglycol ester | | | | | 10.0 |
| Polyester-5 | | | | 3.0 | |
| Phenylbenzimidazole Sulfonic Acid | 2.0 | 2.0 | 2.0 | 2.0 | 2.0 |
| Disteareth-75 IPDI | | | | | |
| Disteareth-100 IPDI | 3.0 | | | | |
| Acrylates/Vinyl Neodecanoate Crosspolymer | | 1.5 | 5.0 | 8.0 | |
| Acrylates/C10-30 Alkyl Acrylate Crosspolymer | | | | | 0.2 |
| Disodium EDTA | 0.2 | 0.2 | 0.2 | 0.2 | 0.2 |
| Methylene Bis-Benzotriazolyl Tetramethylbutylphenol | 5.0 | 5.0 | 5.0 | 5.0 | 5.0 |
| Tromethamine | 0.8 | 0.8 | 0.8 | 0.8 | 0.8 |
| Cyclohexasiloxane (and) Cyclopentasiloxane | 0.8 | 0.8 | 0.8 | 0.8 | 0.8 |
| Phenoxyethanol (and) Methylparaben (and) Ethylparaben (and) Butylparaben (and) Propylparaben (and) Isobutylparaben | 0.8 | 0.8 | 0.8 | 0.8 | 0.8 |
| Tocopheryl Acetate | 0.4 | 0.4 | 0.4 | 0.4 | 0.4 |
| CAS-Regno. 88122-99-0, Ethylhexyl triazone (Octyl triazone; Uvinul T 150) | 1.0 | | | 3.0 | |
| CAS-Regno. 6197-30-4, Octocrylene | | 1.0 | 5.0 | | |
| CAS-Regno. 180898-37-7, Disodium phenyldibenzimidazoletetrasulfonate Neo Heliopan AP or Neo-Heliopan APC | | | | | 2.0 |
| CAS-Regno. 68890-66-4, Octopirox | 1.0 | | | | |
| Tinogard TT (INCI Tetradibutyl Pentaerithrityl Hydroxy-hydrocinnamate) | 3.0 | | | | 1.0 |
| Tinogard HS (INCI Sodium Benzotriazolyl Butylphenol Sulfonate) | | 3.0 | | | |
| compound (BT-01) (INCI Benzotriazolyl Dodecyl p-Cresol) | 0.5 | 1.0 | 3.0 | 0.9 | 1.0 |

| Example B16: High Protection Sunscreen | | | | | |
|---|---|---|---|---|---|
| Merocyanine (MC-03) | 0.5 | 0.8 | 1.0 | 0.3 | 0.33 |
| Tinogard AS (INCI Bumetrizole) | | | | 1.0 | 1.0 |
| Tris(tetramethylhydroxypiperidinol) citrate Compound (ESS-01) | | | | 0.5 | 0.5 |
| 220410-74-2 4-Piperidinol, 1-hydroxy-2,2,6,6-tetramethyl-, 2-hydroxy-1,2,3-propanetricarboxylate (3:1) (salt) | | | 1.0 | | |
| CAS-Regno. 1750-49-8, N-(2-Hydroxypropyl)urea | | 10.0 | | | |
| CAS-Regno. 2078-71-9, N-(2-Hydroxyethyl)urea | 10.0 | | | | |
| mixture of n-butylphthalimide and isopropylphthalimide | | | | | 3.0 |

| Example B17: High Protection Sunscreen | | | | |
|---|---|---|---|---|
| High protection sunscreen (3) INCI-Name | A % w/w | B % w/w | C % w/w | D % w/w |
| Synthetic Beeswax | 0.5 | 0.5 | 0.5 | 0.5 |
| Ethylhexyl Methoxycinnamate | 9.8 | 9.8 | 9.8 | 9.8 |
| Isoamyl p-Methoxycinnamate | 2.0 | 2.0 | 2.0 | 2.0 |
| Ethylhexyl Salicylate | 5.0 | 5.0 | 5.0 | 5.0 |
| Butyl Methoxydibenzoylmethane | 4.0 | 4.0 | 4.0 | 4.0 |
| 4-Methylbenzylidene Camphor | 4.0 | 4.0 | 4.0 | 4.0 |
| Bis-Ethylhexyloxyphenol Methoxyphenyl Triazine | 2.0 | 3.0 | 2.0 | 1.0 |
| Octadecene/MA Copolymer (and) Methyl Acethyl Ricinoleate (and) Di-methylhepthyl Adipate | | 3.0 | | |
| C30-38 olefin/isopropyl maleate/MA copolymer | | | 2.0 | |
| Hydrogenated Dimer Dilinoleyl/Dimethylcarbonate Copolymer | | | | 3.0 |
| Dimethicone | 4.5 | 4.5 | 4.5 | 4.5 |
| C20-22 Alkyl Phosphate (and) C20-22 Alcohols | | 3.0 | | |
| Candelilla/Jojoba/Rice Bran Polyglyceryl-3 esters (and) glyceryl stearate (and) Cetearyl alcohol (and) Sodium stearoyl lactylate | | | 4.0 | |
| Glyceryl oleate citrate (and) Caprylic/Capric Triglycerides | | | | 6.0 |
| Cetearyl Alcohol (and) Dicetyl Phosphate (and) Ceteth-10 Phosphate | 4.5 | | | |
| Cetyl Ricinoleate | 3.0 | 3.0 | 3.0 | 3.0 |
| Pentaerythrityl Distearate | | 1.5 | | |
| Glyceryl Dibehenate (and) Tribehenin (and) Glyceryl Behenate | | | 2.0 | |
| Hydroxypropyl Dimethicone Behenate | 2.2 | 1.0 | | 2.2 |
| Decyl Cocoate | 1.0 | 1.0 | 1.0 | 1.0 |
| Aqua | Qs to 100 | Qs to 100 | Qs to 100 | Qs to 100 |
| Propylene Glycol | 3.0 | 3.0 | 3.0 | 3.0 |
| Methylene Bis-Benzotriazolyl Tetramethyl-butylphenol (and) Aqua (and) Decyl Glucoside (and) Propylene Glycol (and) Xanthan Gum | 5.0 | 4.0 | 6.0 | 8.0 |
| Decyl Glucoside | 0.5 | 0.5 | 0.5 | 0.5 |
| Acrylates/Vinyl Neodecanoate Crosspolymer | | | | |
| Ammonium Acryloyldimethyltaurate/VP Copolymer | 0.3 | 0.3 | 0.3 | 0.3 |
| Phenylbenzimidazole Sulfonic Acid | 2.0 | 2.0 | 2.0 | 2.0 |
| Disteareth-75 IPDI | | 0.3 | 3.0 | |
| Disteareth-100 IPDI | | | | 0.3 |
| Acrylates/C10-30 Alkyl Acrylate Crosspolymer | 0.2 | | | |
| Disodium EDTA | 0.2 | 0.2 | 0.2 | 0.2 |
| Tromethamine | 0.8 | 0.8 | 0.8 | 0.8 |
| Cyclohexasiloxane (and) Cyclopentasiloxane | 0.8 | 0.8 | 0.8 | 0.8 |
| Phenoxyethanol (and) Methylparaben (and) Ethylparaben (and) Butylparaben (and) Propylparaben (and) Isobutylparaben | 0.8 | 0.8 | 0.8 | 0.8 |
| Tocopheryl Acetate | 0.4 | 0.4 | 0.4 | 0.4 |
| CAS-Regno. 88122-99-0, Ethylhexyl triazone (Octyl triazone; Uvinul T 150) | 2.0 | 1.5 | 2.0 | |
| CAS-Regno. 6197-30-4, Octocrylene | 3.0 | 4.0 | 5.0 | |
| CAS-Regno. 180898-37-7, Disodium phenyldibenzimidazoletetrasulfonate Neo Heliopan AP or Neo-Heliopan APC | 3.0 | 4.0 | 5.0 | 3.0 |
| CAS-Regno. 302776-68-7, Uvinul A Plus | 4.0 | | 5.0 | |
| CAS-Regno. 444811-29-4, Propanedioic acid, [(4- | 3.0 | | 1.0 | |

| Example B17: High Protection Sunscreen | | | | |
|---|---|---|---|---|
| High protection sunscreen (3) INCI-Name | A % w/w | B % w/w | C % w/w | D % w/w |
| hydroxy-3,5-dimethoxyphenyl)methylene]-, bis(2-ethylhexyl) ester (Oxynex ST) | | | | |
| CAS-Regno. 477844-93-2, Octofluorene 2-phenylethylbenzoate | | 3.0 1.0 | 1.0 1.0 | |
| CAS-Regno. 68890-66-4, Octopirox | 2.0 | | | 3.0 |
| Tinogard TT (INCI Tetradibutyl Pentaerithrityl Hydroxy-hydrocinnamate) | 1.0 | | 1.0 | 1.0 |
| Tinogard HS (INCI Sodium Benzotriazolyl Butylphenol Sulfonate) | | 2.0 | 3.0 | |
| compound (BT-01) (INCI Benzotriazolyl Dodecyl p-Cresol) | 2.0 | 0.9 | 1.0 | 1.0 |
| Merocyanine (MC-03) | 1.0 | 0.9 | 0.3 | 0.3 |
| Cibafast H Liquid (INCI Sodium Benzotriazolyl Butylphenol Sulfonate, Buteth-3, Tributyl Citrate) | 1.0 | | | |
| Tinogard AS (INCI Bumetrizole) | 2.0 | | 1.0 | |
| CAS-Regn. 30538-92-2 (Compound ESS-06) | 0.05 | | 0.01 | |
| 220410-74-2 4-Piperidinol, 1-hydroxy-2,2,6,6-tetramethyl-, 2-hydroxy-1,2,3-propanetricarboxylate (3:1) (salt) | | | 1.0 | |
| CAS-Regno. 1750-49-8, N-(2-Hydroxypropyl)urea | | 5.0 | | |
| CAS-Regno. 2078-71-9, N-(2-Hydroxyethyl)urea | | | 10.0 | |
| mixture of n-butylphthalimide and isopropylphthalimide | 0.5 | | | 5.0 |

The invention claimed is:

1. A stabilizing composition for the protection of body care and household products against the deleterious effects of light, heat and oxygen comprising
   (a) an effective stabilizing amount of a merocyanine derivative

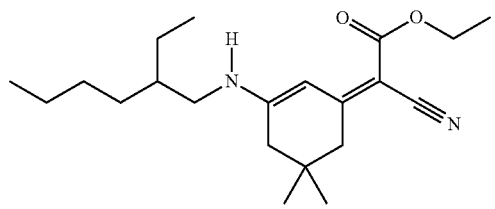

having an absorption maximum of 350 to 400 nm, and
   (b) at least one UV filter comprising a benzotriazole; and optionally
   (c) at least one excited state quencher; and optionally
   (d) at least one salicylate.

2. A composition according to claim 1, wherein component (b) is at least one benzotriazole of formula (4)

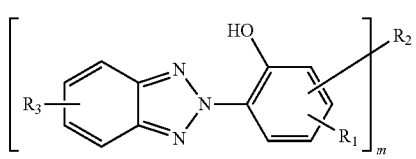

wherein $R_1$ is $C_1$-$C_{30}$alkyl; $C_1$-$C_5$alkoxy; $C_1$-$C_5$alkoxycarbonyl; $C_5$-$C_7$cycloalkyl; $C_6$-$C_{10}$aryl; aralkyl; —$SO_3M$; or a radical of formula (4a);

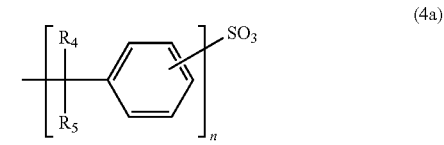

$R_3$ is hydrogen; $C_1$-$C_5$alkyl; $C_1$-$C_5$alkoxy; halogen; or hydroxy;
   $R_4$ and $R_5$ each independently of the other are hydrogen; or $C_1$-$C_5$alkyl;
   m is 1 or 2;
   n is 0 or 1;
   if m=1,
   $R_2$ is hydrogen; unsubstituted or phenyl-substituted $C_1$-$C_{12}$alkyl; or $C_6$-$C_{10}$aryl;
   if m=2,
   $R_2$ is the direct bond; or —$(CH_2)_p$—; and
   p is 1 to 3.

3. A composition according to claim 1, wherein component (b) is at least one benzotriazole of formula (5)

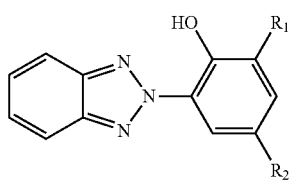

wherein $R_1$ is a random statistical mixture of at least three isomeric branched secondary alkyl groups each having 8 to 30 carbon atoms of the radical

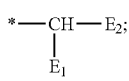

$E_1$ is a straight-chain $C_1$-$C_{14}$alkyl;
$E_2$ is a straight-chain $C_4$-$C_{15}$alkyl; wherein the total number of carbon atoms in $E_1$ plus $E_2$ is from 7 to 29; and
$R_2$ is $C_1$-$C_5$alkyl.

4. A composition according to claim 1, wherein component (b) is 2-(2H-benzotriazol-2-yl)-6-dodecycl-4-methyl-phenol, (BT-01)

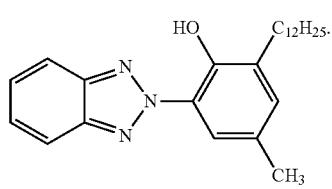

(BT-01)

5. A composition according to claim 1, comprising component (c) which is at least one quencher selected from
($c_1$) hindered nitroxyl compounds of formula (6a);

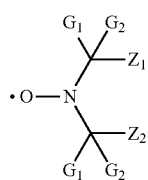

(6a)

($c_2$) hindered hydroxylamine compounds of formula (6b)

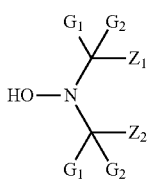

(6b)

and
($c_3$) hindered hydroxylamine salt compounds of formula (6c)

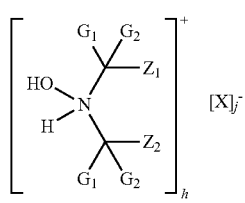

(6c)

wherein
$G_1$ and $G_2$ independently from each other are $C_1$-$C_4$alkyl alkyl; or are together pentamethylene,
$Z_1$ and $Z_2$ are each methyl; or $Z_1$ and $Z_2$ together form a linking moiety which may additionally be substituted by an ester, ether, hydroxy, oxo, cyanohydrine, amide, amino, carboxy or urethane group;

X is an inorganic or organic anion selected from phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an arylsulfonate; and where the total charge of cations h is equal to the total charge of anions j.

6. A composition according to claim 5, wherein component (c) corresponds to a compound of formula (ESS-01)

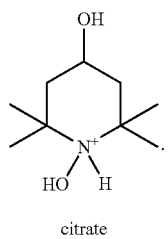

(ESS-01)

citrate

7. A composition according to claim 1, comprising component (d), which is at least one salicylate selected from salicylic acid, homosalate, 2-ethylhexyl salicylate, benzyl salicylate, ethyl salicylate, methyl salicylate, isoamyl salicylate, acetylsalicylic acid and isobutyl salicylate.

8. A composition according to claim 1, wherein
component (b) corresponds to a compound of formula (BT-01)

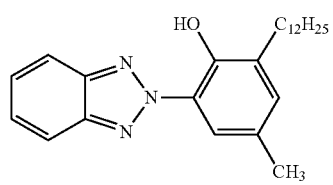

(BT-01)

and
component (c) corresponds to a compound of formula (ESS-01)

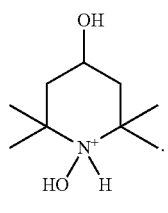

(ESS-01)

citrate

9. A method of protection body care and household products against the deleterious effects of light, heat and oxygen comprising adding to said composition the stabilizing composition according to claim 1.

10. A body-care or a household product comprising a stabilizing composition according to claim 1, wherein the stabilizing composition is present in the body-care or household product in a concentration of about 5 to about 50000 ppm.

11. A stabilizing composition according to claim 1, wherein the weight ratio of component (a) to component (b) is from 20:1 to 1:20.

12. A stabilizing composition according to claim 1, wherein the weight ratio of component (a) to component (c) is from 1:1 to 1000:1.

13. A product according to claim 10,
wherein the body-care product is selected from skin-care products, bath or shower additives, preparations containing fragrances or odoriferous substances, hair-care products, dentifrices, deodorizing or antiperspirant preparations, decorative preparations, light protection formulations and preparations containing active ingredients and
wherein the household product is selected from washing, rinsing or dishwashing agents, shoe polishes, polishing waxes, floor detergents or polishes, all purpose cleaners, bath or toilet cleaners, kitchen cleaners, car shampoos or waxes, neutral, acidic or alkaline cleaners, metal, glass or ceramic cleaners, textile care agents, agents for removing rust, color or stains, stain remover salts, bleaches, furniture or multipurpose polishes, surface protecting formulations, film forming formulations, air care formulations and candles.

14. The method according to claim 9, wherein component (b) is at least one benzotriazole of formula (4)

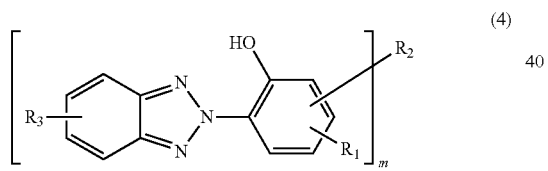

wherein
$R_1$ is $C_1$-$C_{30}$alkyl; $C_1$-$C_3$alkoxy; $C_1$-$C_3$alkoxycarbonyl; $C_5$-$C_7$cycloalkyl; $C_6$-$C_{10}$aryl; aralkyl; —$SO_3M$; or a radical of formula (4a);

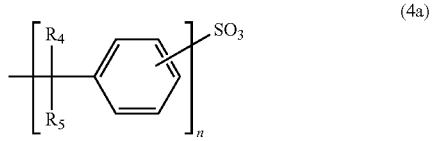

$R_3$ is hydrogen; $C_1$-$C_3$alkyl; $C_1$-$C_3$alkoxy; halogen; or hydroxy;
$R_4$ and $R_5$ each independently of the other are hydrogen; or $C_1$-$C_3$alkyl;
m is 1 or 2;
n is 0 or 1;
if m=1,
$R_2$ is hydrogen; unsubstituted or phenyl-substituted $C_1$-$C_{12}$alkyl; or $C_6$-$C_{10}$aryl;

if m=2,
$R_2$ is the direct bond; or —$(CH_2)_p$—; and
p is 1 to 3.

15. The method according to claim 9, wherein component (b) is at least one benzotriazole of formula (5)

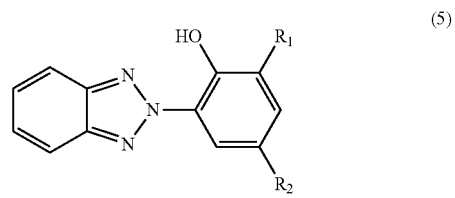

wherein
$R_1$ is a random statistical mixture of at least three isomeric branched secondary alkyl groups each having 8 to 30 carbon atoms of the radical

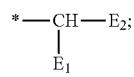

$E_1$ is a straight-chain $C_1$-$C_{14}$alkyl;
$E_2$ is a straight-chain $C_4$-$C_{15}$alkyl; wherein the total number of carbon atoms in $E_1$ plus $E_2$ is from 7 to 29; and
$R_2$ is $C_1$-$C_5$alkyl.

16. The method according to claim 9, wherein component (b) is 2-(2H-benzotriazol-2-yl)-6-dodecycl-4-methyl-phenol, (BT-01)

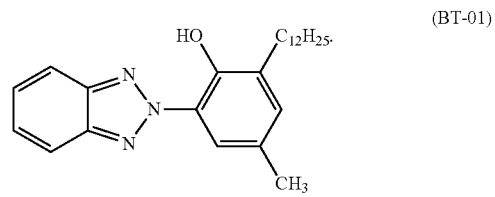

17. The method according to claim 9, wherein component (c) which is at least one quencher is selected from
($c_1$) hindered nitroxyl compounds of formula (6a);

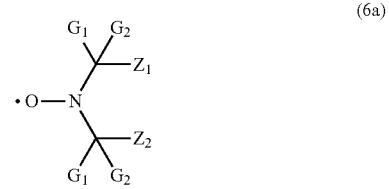

($c_2$) hindered hydroxylamine compounds of formula (6b)

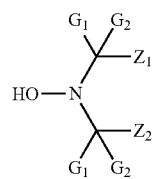

(6b)

and
($c_3$) hindered hydroxylamine salt compounds of formula (6c)

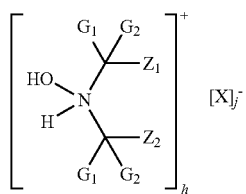

(6c)

wherein
- $G_1$ and $G_2$ independently from each other are $C_1$-$C_4$alkyl alkyl; or are together pentamethylene,
- $Z_1$ and $Z_2$ are each methyl; or $Z_1$ and $Z_2$ together form a linking moiety which may additionally be substituted by an ester, ether, hydroxy, oxo, cyanohydrine, amide, amino, carboxy or urethane group;
- X is an inorganic or organic anion selected from phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, a carboxylate of nitrilotriacetic acid, hydroxyethylethylenediaminetriacetic acid, ethylenediaminetetraacetic acid or of diethylenetriaminepentaacetic acid, a diethylenetriaminepentamethylenephosphonate, an alkylsulfonate or an arylsulfonate; and
- where the total charge of cations h is equal to the total charge of anions j.

18. The method according to claim 9, wherein component (c) corresponds to a compound of formula (ESS-01)

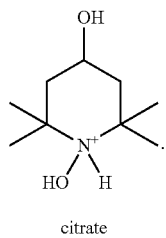

(ESS-01)

citrate

19. The method according to claim 9, wherein component (d), is at least one salicylate selected from salicylic acid, homosalate, 2-ethylhexyl salicylate, benzyl salicylate, ethyl salicylate, methyl salicylate, isoamyl salicylate, acetylsalicylic acid and isobutyl salicylate.

20. The method according to claim 9, wherein the stabilizing composition is present in the body-care or household product in a concentration of about 5 to about 50000 ppm.

* * * * *